(12) United States Patent
Ravis et al.

(10) Patent No.: US 10,154,968 B2
(45) Date of Patent: *Dec. 18, 2018

(54) BUPRENORPHINE NANOPARTICLE COMPOSITION AND METHODS THEREOF

(71) Applicant: AUBURN UNIVERSITY, Auburn, AL (US)

(72) Inventors: William R. Ravis, Auburn, AL (US); Yuh-Jing Lin, Auburn, AL (US)

(73) Assignee: AUBURN UNIVERSITY, Auburn, AL (US)

(*) Notice: Subject to any disclaimer, the term of this patent is extended or adjusted under 35 U.S.C. 154(b) by 0 days.

This patent is subject to a terminal disclaimer.

(21) Appl. No.: 15/428,482

(22) Filed: Feb. 9, 2017

(65) Prior Publication Data
US 2017/0151180 A1 Jun. 1, 2017

Related U.S. Application Data

(63) Continuation of application No. 14/378,706, filed as application No. PCT/US2013/027109 on Feb. 21, 2013, now Pat. No. 9,566,241.

(60) Provisional application No. 61/601,164, filed on Feb. 21, 2012.

(51) Int. Cl.
| A61K 9/51 | (2006.01) |
| A61K 31/485 | (2006.01) |
| A61K 9/00 | (2006.01) |
| A61K 9/16 | (2006.01) |
| A61K 31/4748 | (2006.01) |

(52) U.S. Cl.
CPC .......... *A61K 9/5153* (2013.01); *A61K 9/0019* (2013.01); *A61K 9/0029* (2013.01); *A61K 9/1647* (2013.01); *A61K 31/4748* (2013.01); *A61K 31/485* (2013.01)

(58) Field of Classification Search
None
See application file for complete search history.

(56) References Cited

U.S. PATENT DOCUMENTS

| 5,472,712 | A | 12/1995 | Oshlack et al. |
| 5,486,362 | A | 1/1996 | Kitchell et al. |
| 6,001,800 | A | 12/1999 | Mehta et al. |
| 6,235,710 | B1 | 5/2001 | Mehta et al. |
| 6,905,709 | B2 | 6/2005 | Oshlack et al. |
| 7,316,821 | B2 | 1/2008 | Oshlack et al. |
| 7,473,431 | B2 | 1/2009 | Tice et al. |
| 7,736,665 | B2 | 6/2010 | Patel et al. |
| 9,566,241 | B2 | 2/2017 | Ravis et al. |
| 2003/0138490 | A1 | 7/2003 | Hu et al. |
| 2004/0228917 | A1 | 11/2004 | Oshlack et al. |
| 2005/0048115 | A1 | 3/2005 | Mangena et al. |
| 2006/0073102 | A1 | 4/2006 | Huaihung et al. |
| 2007/0190160 | A1 | 8/2007 | Turos et al. |
| 2008/0099938 | A1* | 5/2008 | Mandal .......... 264/4.1 |
| 2008/0267876 | A1* | 10/2008 | Benita .......... A61K 9/1647 424/9.1 |
| 2010/0239632 | A1* | 9/2010 | Walsh .......... A61K 9/0024 424/423 |
| 2011/0106006 | A1 | 5/2011 | Martin et al. |
| 2011/0159048 | A1 | 6/2011 | Crain et al. |
| 2011/0275616 | A1 | 11/2011 | Sadee et al. |
| 2011/0318331 | A1 | 12/2011 | Wang et al. |
| 2012/0009260 | A1 | 1/2012 | Schobel et al. |
| 2012/0021036 | A1 | 1/2012 | Majeti et al. |
| 2012/0064142 | A1 | 3/2012 | Pillay et al. |
| 2012/0142648 | A1 | 6/2012 | Biggs et al. |
| 2012/0142747 | A1 | 6/2012 | Wilsey et al. |
| 2012/0201761 | A1 | 8/2012 | Sackler |
| 2012/0201888 | A1 | 8/2012 | Bosse et al. |
| 2012/0201895 | A1 | 8/2012 | Matthews et al. |
| 2012/0231069 | A1 | 9/2012 | Nowotnik et al. |
| 2012/0231075 | A1 | 9/2012 | Kao et al. |
| 2012/0237570 | A1 | 9/2012 | Crain et al. |
| 2012/0308614 | A1 | 12/2012 | Moulin et al. |

(Continued)

FOREIGN PATENT DOCUMENTS

| EP | 0754034 | 1/1997 |
| WO | 2011/154724 | 12/2011 |

OTHER PUBLICATIONS

Arakawa et al., Pharm. Res. 8(3):285-291 (1991).
Broadhead et al., "The Spray Drying of Pharmaceuticals," Drug Dev. Ind. Pharm., 18 (11 & 12), pp. 1169-1206 (1992).
Mandal, T.K., "Development of Biodegradable Drug Delivery System to Treat Addiction," Drug Development and Industrial Pharmacy, vol. 25, pp. 773-779, May 18, 1999.

(Continued)

*Primary Examiner* — Susan T Tran
(74) *Attorney, Agent, or Firm* — Barnes & Thornburg LLP

(57) ABSTRACT

Stable nanoparticle compositions comprising buprenorphine and at least one biodegradable polymer. The disclosure also provides methods of controlling pain in an animal and methods of treating addiction in a human utilizing the stable nanoparticle compositions, as well as pharmaceutical formulations comprising the stable nanoparticle compositions. The stable nanoparticle compositions are capable of releasing buprenorphine over several days, weeks, or months following administration. The stable nanoparticle compositions of buprenorphine utilize biodegradable polymers capable of degrading into non-toxic components in the body of an animal and may be excreted in the urine of the animal following their metabolism in the body. The stable nanoparticle compositions can advantageously provide sustained release of buprenorphine in the body after a single administration without the need for surgical removal of implanted matrices subsequent to depletion of the drug.

20 Claims, 2 Drawing Sheets

(56) References Cited

U.S. PATENT DOCUMENTS

2012/0308654 A1 12/2012 Bartholomaus et al.
2013/0011445 A1 1/2013 Crawford et al.
2014/0363487 A1 12/2014 Hille

OTHER PUBLICATIONS

PCT Search Report and Written Opinion for PCT/US2013/027109, dated Mar. 28, 2013.
Pikal, M., Biopharm. 3(9)26-30 (1990).

* cited by examiner

BUPRENORPHINE NANOPARTICLE COMPOSITION AND METHODS THEREOF

CROSS-REFERENCE TO RELATED APPLICATIONS

This application is a continuation application of U.S. application Ser. No. 14/378,706, which is a national stage entry under 35 USC § 371(b) of PCT International Application No. PCT/US2013/027109, filed Feb. 21, 2013, which claims the benefit under 35 USC § 119(e) of U.S. Provisional Application Ser. No. 61/601,164, filed on Feb. 21, 2012, the entire disclosures of which are incorporated herein by reference.

TECHNICAL FIELD

The invention relates to stable nanoparticle compositions of buprenorphine and at least one biodegradable polymer. The invention includes compositions, methods, and formulations for the treatment of disease, such as for controlling pain and addiction in animals.

BACKGROUND AND SUMMARY OF THE INVENTION

Buprenorphine is a semi-synthetic opiate used as an analgesic and for the treatment of addiction to heroin and other opiates. Buprenorphine is classified as a "partial agonist" with a mechanism of action similar to classical mu agonists such as morphine. Buprenorphine exerts an analgesic effect through high affinity binding to mu subclass opiate receptors in the central nervous system of animals.

Buprenorphine has a relatively short half-life of approximately two hours, and the oral absorption of buprenorphine is low as a result of a high first-pass effect in animals. Currently approved dosage forms of buprenorphine include sublingual tablets, transdermal patches, and parenteral formulations. However, the currently available formulations of buprenorphine are undesirable for a variety of reasons. For example, the sublingual tablets can be easily abused by patients and may produce psychological dependence when used chronically. Furthermore, transdermal patches require special procedures for application and disposal, and also possess a low bioavailability in patients. Finally, the currently available parenteral formulations require frequent administration via injections to the patient, sometimes as frequently as four to six injections per day.

Therefore, there exists a need for new compositions and formulations that provide sustained release of buprenorphine following administration. Moreover, new and effective methods of controlling pain and treating addiction in animals utilizing buprenorphine compositions and formulations over a prolonged period of time are also very desirable. Accordingly, the present disclosure provides stable nanoparticle compositions and formulations of buprenorphine and methods of using the compositions and formulations, which exhibit desirable properties and provide related advantages for improvement in administration and treatment of animals with buprenorphine.

The present disclosure provides stable nanoparticle compositions comprising buprenorphine and at least one biodegradable polymer. The disclosure also provides methods of controlling pain in an animal and methods of treating addiction in a human utilizing the stable nanoparticle compositions, as well as pharmaceutical formulations comprising the stable nanoparticle compositions.

The stable nanoparticle compositions, pharmaceutical formulations, and methods comprising buprenorphine according to the present disclosure provide several advantages compared to other compositions, formulations, and methods known in the art. First, the stable nanoparticle compositions are able to provide sustained or prolonged release of buprenorphine. In particular, the stable nanoparticle compositions are capable of releasing buprenorphine over several days, weeks, or months following administration. In comparison, most currently available sustained or extended release dosage forms of buprenorphine can only release the drug over one or two days.

Second, the stable nanoparticle compositions of buprenorphine utilize biodegradable polymers capable of degrading into non-toxic components in the body of an animal and may be excreted in the urine of the animal following their metabolism in the body. Accordingly, the stable nanoparticle compositions can advantageously provide sustained release of buprenorphine in the body after a single administration without the need for surgical removal of implanted matrices subsequent to depletion of the drug.

Third, the stable nanoparticle compositions of buprenorphine can advantageously provide improved adherence of patients in need of treatment due to the lower frequency of administration. In addition, the lower frequency of administering the drug may lessen the incidence of overdose, misuse, or abuse of buprenorphine by patients.

Fourth, the stable nanoparticle compositions are capable of providing a linear releasing profile (i.e., a zero order release profile) of buprenorphine after initial rapid release. In contrast, other buprenorphine compositions such as microspheres possess a multiple phase releasing profile, which can lead to undesirable variability following administration of buprenorphine to animals. Furthermore, the releasing profile of the stable nanoparticle compositions of buprenorphine was unexpectedly consistent regardless of the drug to polymer ratio present in the nanoparticles.

Fifth, the stable nanoparticle compositions of buprenorphine possess an unexpectedly high drug to polymer ratio, high drug loading ratio, and high yield. Furthermore, the stable nanoparticle compositions of buprenorphine may possess unexpectedly greater burst effects of buprenorphine and thus could potentially be used as a loading dose in animals or for a formulation intended for a short-term release of drug.

Finally, the stable nanoparticle compositions of buprenorphine can be tailored in a formulation with a specific dose and release duration depending on the desired characteristics. In contrast, other formulations of buprenorphine purporting to provide sustained release cannot be specifically formulated to provide individualized results.

The following numbered embodiments are contemplated and are non-limiting:

1. A stable nanoparticle composition comprising buprenorphine and at least one biodegradable polymer.

2. The stable nanoparticle composition of clause 1, wherein the biodegradable polymer is selected from the group consisting of polycaprolactone (PCL), polyglycolic acid (PGA), poly(DL)-lactide (PLA), poly(DL)-lactide-co-glycolide (PLGA), or mixtures thereof.

3. The stable nanoparticle composition of clause 1, wherein the biodegradable polymer is PLA.

4. The stable nanoparticle composition of clause 1, wherein the biodegradable polymer is PLGA.

5. The stable nanoparticle composition of clause 1, wherein the biodegradable polymer is PCL.

6. The stable nanoparticle composition of clause 1, wherein the biodegradable polymer is PGA.

7. The stable nanoparticle composition of clause 1, wherein stable nanoparticle composition comprises more than one biodegradable polymer.

8. The stable nanoparticle composition of clause 7, wherein the stable nanoparticle composition comprises two biodegradable polymers.

9. The stable nanoparticle composition of clause 8, wherein the ratio of the first biodegradable polymer to the second biodegradable polymer is in a range between about 1:99 to about 99:1.

10. The stable nanoparticle composition of clause 8, wherein the ratio of the first biodegradable polymer to the second biodegradable polymer is in a range between about 5:95 to about 95:5.

11. The stable nanoparticle composition of clause 8, wherein the ratio of the first biodegradable polymer to the second biodegradable polymer is in a range between about 10:90 to about 90:10.

12. The stable nanoparticle composition of clause 8, wherein the ratio of the first biodegradable polymer to the second biodegradable polymer is in a range between about 15:85 to about 85:15.

13. The stable nanoparticle composition of clause 8, wherein the ratio of the first biodegradable polymer to the second biodegradable polymer is in a range between about 20:80 to about 80:20.

14. The stable nanoparticle composition of clause 8, wherein the ratio of the first biodegradable polymer to the second biodegradable polymer is in a range between about 25:75 to about 75:25.

15. The stable nanoparticle composition of clause 8, wherein the ratio of the first biodegradable polymer to the second biodegradable polymer is in a range between about 30:70 to about 70:30.

16. The stable nanoparticle composition of clause 8, wherein the ratio of the first biodegradable polymer to the second biodegradable polymer is in a range between about 35:65 to about 65:35.

17. The stable nanoparticle composition of clause 8, wherein the ratio of the first biodegradable polymer to the second biodegradable polymer is in a range between about 40:60 to about 60:40.

18. The stable nanoparticle composition of clause 8, wherein the ratio of the first biodegradable polymer to the second biodegradable polymer is in a range between about 45:55 to about 55:45.

19. The stable nanoparticle composition of clause 8, wherein the ratio of the first biodegradable polymer to the second biodegradable polymer is about 10:90.

20. The stable nanoparticle composition of clause 8, wherein the ratio of the first biodegradable polymer to the second biodegradable polymer is about 15:85.

21. The stable nanoparticle composition of clause 8, wherein the ratio of the first biodegradable polymer to the second biodegradable polymer is about 25:75.

22. The stable nanoparticle composition of clause 8, wherein the ratio of the first biodegradable polymer to the second biodegradable polymer is about 50:50.

23. The stable nanoparticle composition of clause 8, wherein the ratio of the first biodegradable polymer to the second biodegradable polymer is about 75:25.

24. The stable nanoparticle composition of clause 8, wherein the ratio of the first biodegradable polymer to the second biodegradable polymer is about 85:15.

25. The stable nanoparticle composition of clause 8, wherein the ratio of the first biodegradable polymer to the second biodegradable polymer is about 90:10.

26. The stable nanoparticle composition of any one of clauses 7 to 25, wherein one biodegradable polymer is PLA.

27. The stable nanoparticle composition of any one of clauses 7 to 26, wherein one biodegradable polymer is PLGA.

28. The stable nanoparticle composition of any one of clauses 7 to 27, wherein one biodegradable polymer is PCL.

29. The stable nanoparticle composition of any one of clauses 7 to 28, wherein one biodegradable polymer is PGA.

30. The stable nanoparticle composition of clause 8, wherein the first biodegradable polymer is PLA and the second biodegradable polymer is PLGA.

31. The stable nanoparticle composition of any one of clauses 1 to 30, wherein at least one biodegradable polymer is conjugated to poly(ethylene) glycol.

32. The stable nanoparticle composition of any one of clauses 1 to 31, wherein the ratio of buprenorphine:polymer is in a range between about 10:1 to about 1:50.

33. The stable nanoparticle composition of any one of clauses 1 to 31, wherein the ratio of buprenorphine:polymer is in a range between about 10:1 to about 1:30.

34. The stable nanoparticle composition of any one of clauses 1 to 31, wherein the ratio of buprenorphine:polymer is in a range between about 10:1 to about 1:20.

35. The stable nanoparticle composition of any one of clauses 1 to 31, wherein the ratio of buprenorphine:polymer is in a range between about 10:1 to about 1:10.

36. The stable nanoparticle composition of any one of clauses 1 to 31, wherein the ratio of buprenorphine:polymer is about 1:1.

37. The stable nanoparticle composition of any one of clauses 1 to 31, wherein the ratio of buprenorphine:polymer is about 1:2.

38. The stable nanoparticle composition of any one of clauses 1 to 31, wherein the ratio of buprenorphine:polymer is about 1:4.

39. The stable nanoparticle composition of any one of clauses 1 to 31, wherein the ratio of buprenorphine:polymer is about 1:5.

40. The stable nanoparticle composition of any one of clauses 1 to 31, wherein the ratio of buprenorphine:polymer is about 1:8.

41. The stable nanoparticle composition of any one of clauses 1 to 31, wherein the ratio of buprenorphine:polymer is about 1:10.

42. The stable nanoparticle composition of any one of clauses 1 to 31, wherein the ratio of buprenorphine:polymer is about 1:15.

43. The stable nanoparticle composition of any one of clauses 1 to 31, wherein the ratio of buprenorphine:polymer is about 1:16.

44. The stable nanoparticle composition of any one of clauses 1 to 31, wherein the ratio of buprenorphine:polymer is about 1:20.

45. The stable nanoparticle composition of any one of clauses 1 to 31, wherein the ratio of buprenorphine:polymer is about 1:25.

46. The stable nanoparticle composition of any one of clauses 1 to 31, wherein the ratio of buprenorphine:polymer is about 1:30.

47. The stable nanoparticle composition of any one of clauses 1 to 31, wherein the ratio of buprenorphine:polymer is about 1:32.

48. The stable nanoparticle composition of any one of clauses 1 to 31, wherein the ratio of buprenorphine:polymer is about 1:48.

49. The stable nanoparticle composition of any one of clauses 1 to 31, wherein the ratio of buprenorphine:polymer is about 1:50.

50. The stable nanoparticle composition of any one of clauses 1 to 49, wherein the amount of buprenorphine is present at a range between about 0.001 to about 1000 mg.

51. The stable nanoparticle composition of any one of clauses 1 to 49, wherein the amount of buprenorphine is present at a range between about 0.001 to about 100 mg.

52. The stable nanoparticle composition of any one of clauses 1 to 49, wherein the amount of buprenorphine is present at a range between about 0.1 to about 100 mg.

53. The stable nanoparticle composition of any one of clauses 1 to 49, wherein the stable nanoparticle composition has a diameter from about 0.5 nm to about 1000 nm.

54. The stable nanoparticle composition of any one of clauses 1 to 49, wherein the stable nanoparticle composition has a diameter between about 10 nm to about 500 nm.

55. The stable nanoparticle composition of any one of clauses 1 to 49, wherein the stable nanoparticle composition has a diameter between about 100 nm to about 500 nm.

56. The stable nanoparticle composition of any one of clauses 1 to 49, wherein the stable nanoparticle composition has a diameter between about 200 nm to about 400 nm.

57. The stable nanoparticle composition of any one of clauses 1 to 49, wherein the stable nanoparticle composition has a diameter of about 100 nm.

58. The stable nanoparticle composition of any one of clauses 1 to 49, wherein the stable nanoparticle composition has a diameter of about 200 nm.

59. The stable nanoparticle composition of any one of clauses 1 to 49, wherein the stable nanoparticle composition has a diameter of about 300 nm.

60. The stable nanoparticle composition of any one of clauses 1 to 49, wherein the stable nanoparticle composition has a diameter of about 400 nm.

61. The stable nanoparticle composition of any one of clauses 1 to 49, wherein the stable nanoparticle composition has a diameter of about 500 nm.

62. The stable nanoparticle composition of any one of clauses 1 to 61, further comprising one or more polymers selected from the group consisting of polyvinyl alcohol (PVA), PEG, sorbitan isostearate, sorbitan monopalmitate (Span 40), carboxymethylcellulose, poloxamer 188, polysorbate 20, polysorbate 80, or mixtures thereof.

63. The stable nanoparticle composition of any one of clauses 1 to 62, wherein the stable nanoparticle composition is lyophilized.

64. The stable nanoparticle composition of any one of clauses 1 to 63, wherein the stable nanoparticle composition has a release profile of buprenorphine of at least 24 hours.

65. The stable nanoparticle composition of any one of clauses 1 to 63, wherein the stable nanoparticle composition has a release profile of buprenorphine of at least 48 hours.

66. The stable nanoparticle composition of any one of clauses 1 to 63, wherein the stable nanoparticle composition has a release profile of buprenorphine of at least 72 hours.

67. The stable nanoparticle composition of any one of clauses 1 to 63, wherein the stable nanoparticle composition has a release profile of buprenorphine of at least 96 hours.

68. The stable nanoparticle composition of any one of clauses 1 to 63, wherein the stable nanoparticle composition has a release profile of buprenorphine of at least 7 days.

69. The stable nanoparticle composition of any one of clauses 1 to 63, wherein the stable nanoparticle composition has a release profile of buprenorphine of at least 14 days.

70. The stable nanoparticle composition of any one of clauses 1 to 63, wherein the stable nanoparticle composition has a release profile of buprenorphine of at least 21 days.

71. The stable nanoparticle composition of any one of clauses 1 to 63, wherein the stable nanoparticle composition has a release profile of buprenorphine of at least 28 days.

72. The stable nanoparticle composition of any one of clauses 1 to 63, wherein the stable nanoparticle composition has a release profile of buprenorphine of at least 2 months.

73. The stable nanoparticle composition of any one of clauses 1 to 63, wherein the stable nanoparticle composition has a release profile of buprenorphine of at least 3 months.

74. The stable nanoparticle composition of any one of clauses 1 to 73, wherein the release profile of the stable nanoparticle composition is a linear release profile, optionally after initial rapid release.

75. The stable nanoparticle composition of any one of clauses 1 to 73, wherein the release profile of the stable nanoparticle composition is a non-linear release profile.

76. The stable nanoparticle composition of any one of clauses 1 to 75, wherein an agent is optionally applied to the stable nanoparticle composition.

77. The stable nanoparticle composition of clause 76, wherein the agent is selected from the group consisting of a surfactant, a stabilizer, a biomarker for targeting, or a second active pharmaceutical ingredient (API).

78. The stable nanoparticle composition of any one of clauses 1 to 77, wherein the stable nanoparticle composition is adapted for use as a parenteral formulation.

79. The stable nanoparticle composition of clause 78, wherein the parenteral formulation is a subcutaneous parenteral formulation.

80. The stable nanoparticle composition of clause 78, wherein the parenteral formulation is an intramuscular parenteral formulation.

81. A method of controlling pain in an animal comprising administering to the animal in need thereof a therapeutically effective amount of a stable nanoparticle composition comprising buprenorphine and at least one biodegradable polymer.

82. The method of clause 81, wherein the pain is associated with a surgery performed or to be performed on the animal.

83. The method of clause 81, wherein the pain is acute pain.

84. The method of clause 81, wherein the pain is chronic pain.

85. The method of any one of clauses 81 to 84, wherein the animal is a human.

86. The method of any one of clauses 81 to 84, wherein the animal is an mammal.

87. The method of any one of clauses 81 to 86, wherein the biodegradable polymer is selected from the group consisting of polycaprolactone (PCL), polyglycolic acid (PGA), poly(DL)-lactide (PLA), poly(DL)-lactide-co-glycolide (PLGA), or mixtures thereof.

88. The method of any one of clauses 81 to 86, wherein the biodegradable polymer is PLA.

89. The method of any one of clauses 81 to 86, wherein the biodegradable polymer is PLGA.

90. The method of any one of clauses 81 to 86, wherein the biodegradable polymer is PCL.

91. The method of any one of clauses 81 to 86, wherein the biodegradable polymer is PGA.

92. The method of any one of clauses 81 to 86, wherein stable nanoparticle composition comprises more than one biodegradable polymer.

93. The method of clause 92, wherein the stable nanoparticle composition comprises two biodegradable polymers.

94. The method of clause 93, wherein the ratio of the first biodegradable polymer to the second biodegradable polymer is in a range between about 1:99 to about 99:1.

95. The method of clause 93, wherein the ratio of the first biodegradable polymer to the second biodegradable polymer is in a range between about 5:95 to about 95:5.

96. The method of clause 93, wherein the ratio of the first biodegradable polymer to the second biodegradable polymer is in a range between about 10:90 to about 90:10.

97. The method of clause 93, wherein the ratio of the first biodegradable polymer to the second biodegradable polymer is in a range between about 15:85 to about 85:15.

98. The method of clause 93, wherein the ratio of the first biodegradable polymer to the second biodegradable polymer is in a range between about 20:80 to about 80:20.

99. The method of clause 93, wherein the ratio of the first biodegradable polymer to the second biodegradable polymer is in a range between about 25:75 to about 75:25.

100. The method of clause 93, wherein the ratio of the first biodegradable polymer to the second biodegradable polymer is in a range between about 30:70 to about 70:30.

101. The method of clause 93, wherein the ratio of the first biodegradable polymer to the second biodegradable polymer is in a range between about 35:65 to about 65:35.

102. The method of clause 93, wherein the ratio of the first biodegradable polymer to the second biodegradable polymer is in a range between about 40:60 to about 60:40.

103. The method of clause 93, wherein the ratio of the first biodegradable polymer to the second biodegradable polymer is in a range between about 45:55 to about 55:45.

104. The method of clause 93, wherein the ratio of the first biodegradable polymer to the second biodegradable polymer is about 10:90.

105. The method of clause 93, wherein the ratio of the first biodegradable polymer to the second biodegradable polymer is about 15:85.

106. The method of clause 93, wherein the ratio of the first biodegradable polymer to the second biodegradable polymer is about 25:75.

107. The method of clause 93, wherein the ratio of the first biodegradable polymer to the second biodegradable polymer is about 50:50.

108. The method of clause 93, wherein the ratio of the first biodegradable polymer to the second biodegradable polymer is about 75:25.

109. The method of clause 93, wherein the ratio of the first biodegradable polymer to the second biodegradable polymer is about 85:15.

110. The method of clause 93, wherein the ratio of the first biodegradable polymer to the second biodegradable polymer is about 90:10.

111. The method of any one of clauses 92 to 110, wherein one biodegradable polymer is PLA.

112. The method of any one of clauses 92 to 111, wherein one biodegradable polymer is PLGA.

113. The method of any one of clauses 92 to 112, wherein one biodegradable polymer is PCL.

114. The method of any one of clauses 92 to 113, wherein one biodegradable polymer is PGA.

115. The method of clause 93, wherein the first biodegradable polymer is PLA and the second biodegradable polymer is PLGA.

116. The method of any one of clauses 81 to 115, wherein at least one biodegradable polymer is conjugated to poly (ethylene) glycol.

117. The method of any one of clauses 81 to 116, wherein the ratio of buprenorphine:polymer is in a range between about 10:1 to about 1:50.

118. The method of any one of clauses 81 to 116, wherein the ratio of buprenorphine:polymer is in a range between about 10:1 to about 1:30.

119. The method of any one of clauses 81 to 116, wherein the ratio of buprenorphine:polymer is in a range between about 10:1 to about 1:20.

120. The method of any one of clauses 81 to 116, wherein the ratio of buprenorphine:polymer is in a range between about 10:1 to about 1:10.

121. The method of any one of clauses 81 to 116, wherein the ratio of buprenorphine:polymer is about 1:1.

122. The method of any one of clauses 81 to 116, wherein the ratio of buprenorphine:polymer is about 1:2.

123. The method of any one of clauses 81 to 116, wherein the ratio of buprenorphine:polymer is about 1:4.

124. The method of any one of clauses 81 to 116, wherein the ratio of buprenorphine:polymer is about 1:5.

125. The method of any one of clauses 81 to 116, wherein the ratio of buprenorphine:polymer is about 1:8.

126. The method of any one of clauses 81 to 116, wherein the ratio of buprenorphine:polymer is about 1:10.

127. The method of any one of clauses 81 to 116, wherein the ratio of buprenorphine:polymer is about 1:15.

128. The method of any one of clauses 81 to 116, wherein the ratio of buprenorphine:polymer is about 1:16.

129. The method of any one of clauses 81 to 116, wherein the ratio of buprenorphine:polymer is about 1:20.

130. The method of any one of clauses 81 to 116, wherein the ratio of buprenorphine:polymer is about 1:25.

131. The method of any one of clauses 81 to 116, wherein the ratio of buprenorphine:polymer is about 1:30.

132. The method of any one of clauses 81 to 116, wherein the ratio of buprenorphine:polymer is about 1:32.

133. The method of any one of clauses 81 to 116, wherein the ratio of buprenorphine:polymer is about 1:48.

134. The method of any one of clauses 81 to 116, wherein the ratio of buprenorphine:polymer is about 1:50.

135. The method of any one of clauses 81 to 134, wherein the stable nanoparticle composition is administered to the animal at a dose of about 0.001 to about 1000 mg of buprenorphine per kg of animal body weight.

136. The method of any one of clauses 81 to 134, wherein the stable nanoparticle composition is administered to the animal at a dose of about 0.001 to about 100 mg of buprenorphine per kg of animal body weight.

137. The method of any one of clauses 81 to 134, wherein the stable nanoparticle composition is administered to the animal at a dose of about 0.01 to about 100 mg of buprenorphine per kg of animal body weight.

138. The method of any one of clauses 81 to 134, wherein the stable nanoparticle composition is administered to the animal at a dose of about 0.1 to about 100 mg of buprenorphine per kg of animal body weight.

139. The method of any one of clauses 81 to 134, wherein the stable nanoparticle composition is administered to the animal at a dose of about 0.1 to about 10 mg of buprenorphine per kg of animal body weight.

101. The method of any one of clauses 81 to 134, wherein the stable nanoparticle composition is administered to the animal at a dose of about 1 to about 5 mg of buprenorphine per kg of animal body weight.

102. The method of any one of clauses 81 to 134, wherein the stable nanoparticle composition is administered to the animal at a dose of about 1 mg of buprenorphine per kg of animal body weight.

103. The method of any one of clauses 81 to 134, wherein the stable nanoparticle composition is administered to the animal at a dose of about 2 mg of buprenorphine per kg of animal body weight.

104. The method of any one of clauses 81 to 134, wherein the stable nanoparticle composition is administered to the animal at a dose of about 3 mg of buprenorphine per kg of animal body weight.

105. The method of any one of clauses 81 to 134, wherein the stable nanoparticle composition is administered to the animal at a dose of about 4 mg of buprenorphine per kg of animal body weight.

140. The method of any one of clauses 81 to 134, wherein the stable nanoparticle composition is administered to the animal at a dose of about 5 mg of buprenorphine per kg of animal body weight.

141. The method of any one of clauses 81 to 140, wherein the stable nanoparticle composition has a diameter from about 0.5 nm to about 1000 nm.

142. The method of any one of clauses 81 to 140, wherein the stable nanoparticle composition has a diameter between about 10 nm to about 500 nm.

143. The method of any one of clauses 81 to 140, wherein the stable nanoparticle composition has a diameter between about 100 nm to about 500 nm.

144. The method of any one of clauses 81 to 140, wherein the stable nanoparticle composition has a diameter between about 200 nm to about 400 nm.

145. The method of any one of clauses 81 to 140, wherein the stable nanoparticle composition has a diameter of about 100 nm.

146. The method of any one of clauses 81 to 140, wherein the stable nanoparticle composition has a diameter of about 200 nm.

147. The method of any one of clauses 81 to 140, wherein the stable nanoparticle composition has a diameter of about 300 nm.

148. The method of any one of clauses 81 to 140, wherein the stable nanoparticle composition has a diameter of about 400 nm.

149. The method of any one of clauses 81 to 140, wherein the stable nanoparticle composition has a diameter of about 500 nm.

150. The method of any one of clauses 81 to 149, wherein the stable nanoparticle composition further comprises one or more polymers selected from the group consisting of polyvinyl alcohol (PVA), PEG, sorbitan isostearate, sorbitan monopalmitate (Span 40), carboxymethylcellulose, poloxamer 188, polysorbate 20, polysorbate 80, or mixtures thereof.

151. The method of any one of clauses 81 to 150, wherein the stable nanoparticle composition is lyophilized.

152. The method of any one of clauses 81 to 151, wherein the stable nanoparticle composition has a release profile of buprenorphine of at least 24 hours.

153. The method of any one of clauses 81 to 151, wherein the stable nanoparticle composition has a release profile of buprenorphine of at least 48 hours.

154. The method of any one of clauses 81 to 151, wherein the stable nanoparticle composition has a release profile of buprenorphine of at least 72 hours.

155. The method of any one of clauses 81 to 151, wherein the stable nanoparticle composition has a release profile of buprenorphine of at least 96 hours.

156. The method of any one of clauses 81 to 151, wherein the stable nanoparticle composition has a release profile of buprenorphine of at least 7 days.

157. The method of any one of clauses 81 to 151, wherein the stable nanoparticle composition has a release profile of buprenorphine of at least 14 days.

158. The method of any one of clauses 81 to 151, wherein the stable nanoparticle composition has a release profile of buprenorphine of at least 21 days.

159. The method of any one of clauses 81 to 151, wherein the stable nanoparticle composition has a release profile of buprenorphine of at least 28 days.

160. The method of any one of clauses 81 to 151, wherein the stable nanoparticle composition has a release profile of buprenorphine of at least 2 months.

161. The method of any one of clauses 81 to 151, wherein the stable nanoparticle composition has a release profile of buprenorphine of at least 3 months.

162. The method of any one of clauses 81 to 151, wherein the release profile of the stable nanoparticle composition is a linear release profile, optionally after initial rapid release.

163. The method of any one of clauses 81 to 151, wherein the release profile of the stable nanoparticle composition is a non-linear release profile.

164. The method of any one of clauses 81 to 151, wherein an agent is optionally applied to the stable nanoparticle composition.

165. The method of clause 164, wherein the agent is selected from the group consisting of a surfactant, a stabilizer, a biomarker for targeting, or a second active pharmaceutical ingredient (API).

166. The method of any one of clauses 81 to 165, wherein the stable nanoparticle composition is administered as a single dose.

167. The method of any one of clauses 81 to 166, wherein stable nanoparticle composition is administered as a single unit dose.

168. The method of any one of clauses 81 to 167, wherein the administration is a parenteral administration.

169. The method of clause 168, wherein the parenteral formulation is a subcutaneous parenteral formulation.

170. The method of clause 168, wherein the parenteral formulation is an intramuscular parenteral formulation.

171. A method of treating addiction in a human comprising administering to the animal in need thereof a therapeutically effective amount of a stable nanoparticle composition comprising buprenorphine and at least one biodegradable polymer.

172. The method of clause 171, wherein the addiction is an opiate addiction.

173. The method of clause 171 or clause 172, wherein the biodegradable polymer is selected from the group consisting of polycaprolactone (PCL), polyglycolic acid (PGA), poly (DL)-lactide (PLA), poly(DL)-lactide-co-glycolide (PLGA), or mixtures thereof.

174. The method of clause 171 or clause 172, wherein the biodegradable polymer is PLA.

175. The method of clause 171 or clause 172, wherein the biodegradable polymer is PLGA.

176. The method of clause 171 or clause 172, wherein the biodegradable polymer is PCL.

177. The method of clause 171 or clause 172, wherein the biodegradable polymer is PGA.

178. The method of clause 171 or clause 172, wherein stable nanoparticle composition comprises more than one biodegradable polymer.

179. The method of clause 178, wherein the stable nanoparticle composition comprises two biodegradable polymers.

180. The method of clause 179, wherein the ratio of the first biodegradable polymer to the second biodegradable polymer is in a range between about 1:99 to about 99:1.

181. The method of clause 179, wherein the ratio of the first biodegradable polymer to the second biodegradable polymer is in a range between about 5:95 to about 95:5.

182. The method of clause 179, wherein the ratio of the first biodegradable polymer to the second biodegradable polymer is in a range between about 10:90 to about 90:10.

183. The method of clause 179, wherein the ratio of the first biodegradable polymer to the second biodegradable polymer is in a range between about 15:85 to about 85:15.

184. The method of clause 179, wherein the ratio of the first biodegradable polymer to the second biodegradable polymer is in a range between about 20:80 to about 80:20.

185. The method of clause 179, wherein the ratio of the first biodegradable polymer to the second biodegradable polymer is in a range between about 25:75 to about 75:25.

186. The method of clause 179, wherein the ratio of the first biodegradable polymer to the second biodegradable polymer is in a range between about 30:70 to about 70:30.

187. The method of clause 179, wherein the ratio of the first biodegradable polymer to the second biodegradable polymer is in a range between about 35:65 to about 65:35.

188. The method of clause 179, wherein the ratio of the first biodegradable polymer to the second biodegradable polymer is in a range between about 40:60 to about 60:40.

189. The method of clause 179, wherein the ratio of the first biodegradable polymer to the second biodegradable polymer is in a range between about 45:55 to about 55:45.

190. The method of clause 179, wherein the ratio of the first biodegradable polymer to the second biodegradable polymer is about 10:90.

191. The method of clause 179, wherein the ratio of the first biodegradable polymer to the second biodegradable polymer is about 15:85.

192. The method of clause 179, wherein the ratio of the first biodegradable polymer to the second biodegradable polymer is about 25:75.

193. The method of clause 179, wherein the ratio of the first biodegradable polymer to the second biodegradable polymer is about 50:50.

194. The method of clause 179, wherein the ratio of the first biodegradable polymer to the second biodegradable polymer is about 75:25.

195. The method of clause 179, wherein the ratio of the first biodegradable polymer to the second biodegradable polymer is about 85:15.

196. The method of clause 179, wherein the ratio of the first biodegradable polymer to the second biodegradable polymer is about 90:10.

197. The method of any one of clauses 178 to 196, wherein one biodegradable polymer is PLA.

198. The method of any one of clauses 178 to 197, wherein one biodegradable polymer is PLGA.

199. The method of any one of clauses 178 to 198, wherein one biodegradable polymer is PCL.

200. The method of any one of clauses 178 to 199, wherein one biodegradable polymer is PGA.

201. The method of clause 179, wherein the first biodegradable polymer is PLA and the second biodegradable polymer is PLGA.

202. The method of any one of clauses 171 to 201, wherein at least one biodegradable polymer is conjugated to poly(ethylene) glycol.

203. The method of any one of clauses 171 to 202, wherein the ratio of buprenorphine:polymer is in a range between about 10:1 to about 1:50.

204. The method of any one of clauses 171 to 202, wherein the ratio of buprenorphine:polymer is in a range between about 10:1 to about 1:30.

205. The method of any one of clauses 171 to 202, wherein the ratio of buprenorphine:polymer is in a range between about 10:1 to about 1:20.

206. The method of any one of clauses 171 to 202, wherein the ratio of buprenorphine:polymer is in a range between about 10:1 to about 1:10.

207. The method of any one of clauses 171 to 202, wherein the ratio of buprenorphine:polymer is about 1:1.

208. The method of any one of clauses 171 to 202, wherein the ratio of buprenorphine:polymer is about 1:2.

209. The method of any one of clauses 171 to 202, wherein the ratio of buprenorphine:polymer is about 1:4.

210. The method of any one of clauses 171 to 202, wherein the ratio of buprenorphine:polymer is about 1:5.

211. The method of any one of clauses 171 to 202, wherein the ratio of buprenorphine:polymer is about 1:8.

212. The method of any one of clauses 171 to 202, wherein the ratio of buprenorphine:polymer is about 1:10.

213. The method of any one of clauses 171 to 202, wherein the ratio of buprenorphine:polymer is about 1:15.

214. The method of any one of clauses 171 to 202, wherein the ratio of buprenorphine:polymer is about 1:16.

215. The method of any one of clauses 171 to 202, wherein the ratio of buprenorphine:polymer is about 1:20.

216. The method of any one of clauses 171 to 202, wherein the ratio of buprenorphine:polymer is about 1:25.

217. The method of any one of clauses 171 to 202, wherein the ratio of buprenorphine:polymer is about 1:30.

218. The method of any one of clauses 171 to 202, wherein the ratio of buprenorphine:polymer is about 1:32.

219. The method of any one of clauses 171 to 202, wherein the ratio of buprenorphine:polymer is about 1:48.

220. The method of any one of clauses 171 to 202, wherein the ratio of buprenorphine:polymer is about 1:50.

221. The method of any one of clauses 171 to 220, wherein the stable nanoparticle composition is administered to the animal at a dose of about 0.001 to about 1000 mg of buprenorphine per kg of animal body weight.

222. The method of any one of clauses 171 to 220, wherein the stable nanoparticle composition is administered to the animal at a dose of about 0.001 to about 100 mg of buprenorphine per kg of animal body weight.

223. The method of any one of clauses 171 to 220, wherein the stable nanoparticle composition is administered to the animal at a dose of about 0.01 to about 100 mg of buprenorphine per kg of animal body weight.

224. The method of any one of clauses 171 to 220, wherein the stable nanoparticle composition is administered to the animal at a dose of about 0.1 to about 100 mg of buprenorphine per kg of animal body weight.

225. The method of any one of clauses 171 to 220, wherein the stable nanoparticle composition is administered to the animal at a dose of about 0.1 to about 10 mg of buprenorphine per kg of animal body weight.

226. The method of any one of clauses 171 to 220, wherein the stable nanoparticle composition is administered to the animal at a dose of about 1 to about 5 mg of buprenorphine per kg of animal body weight.

227. The method of any one of clauses 171 to 220, wherein the stable nanoparticle composition is administered to the animal at a dose of about 1 mg of buprenorphine per kg of animal body weight.

228. The method of any one of clauses 171 to 220, wherein the stable nanoparticle composition is administered to the animal at a dose of about 2 mg of buprenorphine per kg of animal body weight.

229. The method of any one of clauses 171 to 220, wherein the stable nanoparticle composition is administered to the animal at a dose of about 3 mg of buprenorphine per kg of animal body weight.

230. The method of any one of clauses 171 to 220, wherein the stable nanoparticle composition is administered to the animal at a dose of about 4 mg of buprenorphine per kg of animal body weight.

231. The method of any one of clauses 171 to 220, wherein the stable nanoparticle composition is administered to the animal at a dose of about 5 mg of buprenorphine per kg of animal body weight.

232. The method of any one of clauses 171 to 231, wherein the stable nanoparticle composition has a diameter from about 0.5 nm to about 1000 nm.

233. The method of any one of clauses 171 to 231, wherein the stable nanoparticle composition has a diameter between about 10 nm to about 500 nm.

234. The method of any one of clauses 171 to 231, wherein the stable nanoparticle composition has a diameter between about 100 nm to about 500 nm.

235. The method of any one of clauses 171 to 231, wherein the stable nanoparticle composition has a diameter between about 200 nm to about 400 nm.

236. The method of any one of clauses 171 to 231, wherein the stable nanoparticle composition has a diameter of about 100 nm.

237. The method of any one of clauses 171 to 231, wherein the stable nanoparticle composition has a diameter of about 200 nm.

238. The method of any one of clauses 171 to 231, wherein the stable nanoparticle composition has a diameter of about 300 nm.

239. The method of any one of clauses 171 to 231, wherein the stable nanoparticle composition has a diameter of about 400 nm.

240. The method of any one of clauses 171 to 231, wherein the stable nanoparticle composition has a diameter of about 500 nm.

241. The method of any one of clauses 171 to 240, wherein the stable nanoparticle composition further comprises one or more polymers selected from the group consisting of polyvinyl alcohol (PVA), PEG, sorbitan isostearate, sorbitan monopalmitate (Span 40), carboxymethylcellulose, poloxamer 188, polysorbate 20, polysorbate 80, or mixtures thereof.

242. The method of any one of clauses 171 to 241, wherein the stable nanoparticle composition is lyophilized.

243. The method of any one of clauses 171 to 242, wherein the stable nanoparticle composition has a release profile of buprenorphine of at least 24 hours.

244. The method of any one of clauses 171 to 242, wherein the stable nanoparticle composition has a release profile of buprenorphine of at least 48 hours.

245. The method of any one of clauses 171 to 242, wherein the stable nanoparticle composition has a release profile of buprenorphine of at least 72 hours.

246. The method of any one of clauses 171 to 242, wherein the stable nanoparticle composition has a release profile of buprenorphine of at least 96 hours.

247. The method of any one of clauses 171 to 242, wherein the stable nanoparticle composition has a release profile of buprenorphine of at least 7 days.

248. The method of any one of clauses 171 to 242, wherein the stable nanoparticle composition has a release profile of buprenorphine of at least 14 days.

249. The method of any one of clauses 171 to 242, wherein the stable nanoparticle composition has a release profile of buprenorphine of at least 21 days.

250. The method of any one of clauses 171 to 242, wherein the stable nanoparticle composition has a release profile of buprenorphine of at least 28 days.

251. The method of any one of clauses 171 to 242, wherein the stable nanoparticle composition has a release profile of buprenorphine of at least 2 months.

252. The method of any one of clauses 171 to 242, wherein the stable nanoparticle composition has a release profile of buprenorphine of at least 3 months.

253. The method of any one of clauses 171 to 242, wherein the release profile of the stable nanoparticle composition is a linear release profile, optionally after initial rapid release.

254. The method of any one of clauses 171 to 242, wherein the release profile of the stable nanoparticle composition is a non-linear release profile.

255. The method of any one of clauses 171 to 242, wherein an agent is optionally applied to the stable nanoparticle composition.

256. The method of clause 255, wherein the agent is selected from the group consisting of a surfactant, a stabilizer, a biomarker for targeting, or a second active pharmaceutical ingredient (API).

257. The method of any one of clauses 171 to 256, wherein stable nanoparticle composition is administered as a single dose.

258. The method of any one of clauses 171 to 257, wherein stable nanoparticle composition is administered as a single unit dose.

259. The method of any one of clauses 171 to 258, wherein the administration is a parenteral administration.

260. The method of clause 259, wherein the parenteral formulation is a subcutaneous parenteral formulation.

261. The method of clause 259, wherein the parenteral formulation is an intramuscular parenteral formulation.

262. A pharmaceutical formulation comprising a therapeutically effective amount of a stable nanoparticle composition, wherein stable nanoparticle composition comprises buprenorphine and at least one biodegradable polymer.

263. The pharmaceutical formulation of clause 262, wherein the pharmaceutical formulation is a parenteral formulation.

264. The pharmaceutical formulation of clause 263, wherein the parenteral formulation is a subcutaneous parenteral formulation.

265. The pharmaceutical formulation of clause 263, wherein the parenteral formulation is an intramuscular parenteral formulation.

266. The pharmaceutical formulation of any one of clauses 262 to 265, wherein the pharmaceutical formulation is suitable for administration at a dose of about 0.001 to about 1000 mg of buprenorphine per kg of animal body weight.

267. The pharmaceutical formulation of any one of clauses 262 to 265, wherein the pharmaceutical formulation is suitable for administration at a dose of about 0.001 to about 100 mg of buprenorphine per kg of animal body weight.

268. The pharmaceutical formulation of any one of clauses 262 to 265, wherein the pharmaceutical formulation is suitable for administration at a dose of about 0.01 to about 100 mg of buprenorphine per kg of animal body weight.

269. The pharmaceutical formulation of any one of clauses 262 to 265, wherein the pharmaceutical formulation is suitable for administration at a dose of about 0.1 to about 100 mg of buprenorphine per kg of animal body weight.

270. The pharmaceutical formulation of any one of clauses 262 to 265, wherein the pharmaceutical formulation is suitable for administration at a dose of about 0.1 to about 10 mg of buprenorphine per kg of animal body weight.

271. The pharmaceutical formulation of any one of clauses 262 to 265, wherein the pharmaceutical formulation is suitable for administration at a dose of about 1 to about 5 mg of buprenorphine per kg of animal body weight.

272. The pharmaceutical formulation of any one of clauses 262 to 265, wherein the pharmaceutical formulation is suitable for administration at a dose of about 2 mg of buprenorphine per kg of animal body weight.

273. The pharmaceutical formulation of any one of clauses 262 to 265, wherein the pharmaceutical formulation is suitable for administration at a dose of about 3 mg of buprenorphine per kg of animal body weight.

274. The pharmaceutical formulation of any one of clauses 262 to 265, wherein the pharmaceutical formulation is suitable for administration at a dose of about 4 mg of buprenorphine per kg of animal body weight.

275. The pharmaceutical formulation of any one of clauses 262 to 265, wherein the pharmaceutical formulation is suitable for administration at a dose of about 5 mg of buprenorphine per kg of animal body weight.

276. The pharmaceutical formulation of any one of clauses 262 to 275, wherein the pharmaceutical formulation is administered once every at least one week.

277. The pharmaceutical formulation of any one of clauses 262 to 275, wherein the pharmaceutical formulation is administered once every at least two weeks.

278. The pharmaceutical formulation of any one of clauses 262 to 275, wherein the pharmaceutical formulation is administered once every at least three weeks.

279. The pharmaceutical formulation of any one of clauses 262 to 275, wherein the pharmaceutical formulation is administered once every at least four weeks.

280. The pharmaceutical formulation of any one of clauses 262 to 275, wherein the pharmaceutical formulation is administered once every at least six weeks.

281. The pharmaceutical formulation of any one of clauses 262 to 275, wherein the pharmaceutical formulation is administered once every at least two months.

282. The pharmaceutical formulation of any one of clauses 262 to 275, wherein the pharmaceutical formulation is administered once every at least three months.

283. The pharmaceutical formulation of any one of clauses 262 to 282, wherein the biodegradable polymer is selected from the group consisting of polycaprolactone (PCL), polyglycolic acid (PGA), poly(DL)-lactide (PLA), poly(DL)-lactide-co-glycolide (PLGA), or mixtures thereof.

284. The pharmaceutical formulation of any one of clauses 262 to 282, wherein the biodegradable polymer is PLA.

285. The pharmaceutical formulation of any one of clauses 262 to 282, wherein the biodegradable polymer is PLGA.

286. The pharmaceutical formulation of any one of clauses 262 to 282, wherein the biodegradable polymer is PCL.

287. The pharmaceutical formulation of any one of clauses 262 to 282, wherein the biodegradable polymer is PGA.

288. The pharmaceutical formulation of any one of clauses 262 to 282, wherein stable nanoparticle composition comprises more than one biodegradable polymer.

289. The pharmaceutical formulation of clause 288, wherein the stable nanoparticle composition comprises two biodegradable polymers.

290. The pharmaceutical formulation of clause 289, wherein the ratio of the first biodegradable polymer to the second biodegradable polymer is in a range between about 1:99 to about 99:1.

291. The pharmaceutical formulation of clause 289, wherein the ratio of the first biodegradable polymer to the second biodegradable polymer is in a range between about 5:95 to about 95:5.

292. The pharmaceutical formulation of clause 289, wherein the ratio of the first biodegradable polymer to the second biodegradable polymer is in a range between about 10:90 to about 90:10.

293. The pharmaceutical formulation of clause 289, wherein the ratio of the first biodegradable polymer to the second biodegradable polymer is in a range between about 15:85 to about 85:15.

294. The pharmaceutical formulation of clause 289, wherein the ratio of the first biodegradable polymer to the second biodegradable polymer is in a range between about 20:80 to about 80:20.

295. The pharmaceutical formulation of clause 289, wherein the ratio of the first biodegradable polymer to the second biodegradable polymer is in a range between about 25:75 to about 75:25.

296. The pharmaceutical formulation of clause 289, wherein the ratio of the first biodegradable polymer to the second biodegradable polymer is in a range between about 30:70 to about 70:30.

297. The pharmaceutical formulation of clause 289, wherein the ratio of the first biodegradable polymer to the second biodegradable polymer is in a range between about 35:65 to about 65:35.

298. The pharmaceutical formulation of clause 289, wherein the ratio of the first biodegradable polymer to the second biodegradable polymer is in a range between about 40:60 to about 60:40.

299. The pharmaceutical formulation of clause 289, wherein the ratio of the first biodegradable polymer to the second biodegradable polymer is in a range between about 45:55 to about 55:45.

300. The pharmaceutical formulation of clause 289, wherein the ratio of the first biodegradable polymer to the second biodegradable polymer is about 10:90.

301. The pharmaceutical formulation of clause 289, wherein the ratio of the first biodegradable polymer to the second biodegradable polymer is about 15:85.

302. The pharmaceutical formulation of clause 289, wherein the ratio of the first biodegradable polymer to the second biodegradable polymer is about 25:75.

303. The pharmaceutical formulation of clause 289, wherein the ratio of the first biodegradable polymer to the second biodegradable polymer is about 50:50.

304. The pharmaceutical formulation of clause 289, wherein the ratio of the first biodegradable polymer to the second biodegradable polymer is about 75:25.

305. The pharmaceutical formulation of clause 289, wherein the ratio of the first biodegradable polymer to the second biodegradable polymer is about 85:15.

306. The pharmaceutical formulation of clause 289, wherein the ratio of the first biodegradable polymer to the second biodegradable polymer is about 90:10.

307. The pharmaceutical formulation of any one of clauses 288 to 306, wherein one biodegradable polymer is PLA.

308. The pharmaceutical formulation of any one of clauses 288 to 307, wherein one biodegradable polymer is PLGA.

309. The pharmaceutical formulation of any one of clauses 288 to 308, wherein one biodegradable polymer is PCL.

310. The pharmaceutical formulation of any one of clauses 288 to 309, wherein one biodegradable polymer is PGA.

311. The pharmaceutical formulation of clause 289, wherein the first biodegradable polymer is PLA and the second biodegradable polymer is PLGA.

312. The pharmaceutical formulation of any one of clauses 262 to 311, wherein at least one biodegradable polymer is conjugated to poly(ethylene) glycol.

313. The pharmaceutical formulation of any one of clauses 262 to 312, wherein the ratio of buprenorphine:polymer is in a range between about 10:1 to about 1:50.

314. The pharmaceutical formulation of any one of clauses 262 to 312, wherein the ratio of buprenorphine:polymer is in a range between about 10:1 to about 1:30.

315. The pharmaceutical formulation of any one of clauses 262 to 312, wherein the ratio of buprenorphine:polymer is in a range between about 10:1 to about 1:20.

316. The pharmaceutical formulation of any one of clauses 262 to 312, wherein the ratio of buprenorphine:polymer is in a range between about 10:1 to about 1:10.

317. The pharmaceutical formulation of any one of clauses 262 to 312, wherein the ratio of buprenorphine:polymer is about 1:1.

318. The pharmaceutical formulation of any one of clauses 262 to 312, wherein the ratio of buprenorphine:polymer is about 1:2.

319. The pharmaceutical formulation of any one of clauses 262 to 312, wherein the ratio of buprenorphine:polymer is about 1:4.

320. The pharmaceutical formulation of any one of clauses 262 to 312, wherein the ratio of buprenorphine:polymer is about 1:5.

321. The pharmaceutical formulation of any one of clauses 262 to 312, wherein the ratio of buprenorphine:polymer is about 1:8.

322. The pharmaceutical formulation of any one of clauses 262 to 312, wherein the ratio of buprenorphine:polymer is about 1:10.

323. The pharmaceutical formulation of any one of clauses 262 to 312, wherein the ratio of buprenorphine:polymer is about 1:15.

324. The pharmaceutical formulation of any one of clauses 262 to 312, wherein the ratio of buprenorphine:polymer is about 1:16.

325. The pharmaceutical formulation of any one of clauses 262 to 312, wherein the ratio of buprenorphine:polymer is about 1:20.

326. The pharmaceutical formulation of any one of clauses 262 to 312, wherein the ratio of buprenorphine:polymer is about 1:25.

327. The pharmaceutical formulation of any one of clauses 262 to 312, wherein the ratio of buprenorphine:polymer is about 1:30.

328. The pharmaceutical formulation of any one of clauses 262 to 312, wherein the ratio of buprenorphine:polymer is about 1:32.

329. The pharmaceutical formulation of any one of clauses 262 to 312, wherein the ratio of buprenorphine:polymer is about 1:48.

330. The pharmaceutical formulation of any one of clauses 262 to 312, wherein the ratio of buprenorphine:polymer is about 1:50.

331. The pharmaceutical formulation of any one of clauses 262 to 330, wherein the stable nanoparticle composition has a diameter from about 0.5 nm to about 1000 nm.

332. The pharmaceutical formulation of any one of clauses 262 to 330, wherein the stable nanoparticle composition has a diameter between about 10 nm to about 500 nm.

333. The pharmaceutical formulation of any one of clauses 262 to 330, wherein the stable nanoparticle composition has a diameter between about 100 nm to about 500 nm.

334. The pharmaceutical formulation of any one of clauses 262 to 330, wherein the stable nanoparticle composition has a diameter between about 200 nm to about 400 nm.

335. The pharmaceutical formulation of any one of clauses 262 to 330, wherein the stable nanoparticle composition has a diameter of about 100 nm.

336. The pharmaceutical formulation of any one of clauses 262 to 330, wherein the stable nanoparticle composition has a diameter of about 200 nm.

337. The pharmaceutical formulation of any one of clauses 262 to 330, wherein the stable nanoparticle composition has a diameter of about 300 nm.

338. The pharmaceutical formulation of any one of clauses 262 to 330, wherein the stable nanoparticle composition has a diameter of about 400 nm.

339. The pharmaceutical formulation of any one of clauses 262 to 330, wherein the stable nanoparticle composition has a diameter of about 500 nm.

340. The pharmaceutical formulation of any one of clauses 262 to 339, wherein the stable nanoparticle composition further comprises one or more polymers selected from the group consisting of polyvinyl alcohol (PVA), PEG, sorbitan isostearate, sorbitan monopalmitate (Span 40), carboxymethylcellulose, poloxamer 188, polysorbate 20, polysorbate 80, or mixtures thereof.

341. The pharmaceutical formulation of any one of clauses 262 to 340, wherein the stable nanoparticle composition is lyophilized.

342. The pharmaceutical formulation of any one of clauses 262 to 341, wherein the stable nanoparticle composition has a release profile of buprenorphine of at least 24 hours.

343. The pharmaceutical formulation of any one of clauses 262 to 341, wherein the stable nanoparticle composition has a release profile of buprenorphine of at least 48 hours.

344. The pharmaceutical formulation of any one of clauses 262 to 341, wherein the stable nanoparticle composition has a release profile of buprenorphine of at least 72 hours.

345. The pharmaceutical formulation of any one of clauses 262 to 341, wherein the stable nanoparticle composition has a release profile of buprenorphine of at least 96 hours.

346. The pharmaceutical formulation of any one of clauses 262 to 341, wherein the stable nanoparticle composition has a release profile of buprenorphine of at least 7 days.

347. The pharmaceutical formulation of any one of clauses 262 to 341, wherein the stable nanoparticle composition has a release profile of buprenorphine of at least 14 days.

348. The pharmaceutical formulation of any one of clauses 262 to 341, wherein the stable nanoparticle composition has a release profile of buprenorphine of at least 21 days.

349. The pharmaceutical formulation of any one of clauses 262 to 341, wherein the stable nanoparticle composition has a release profile of buprenorphine of at least 28 days.

350. The pharmaceutical formulation of any one of clauses 262 to 341, wherein the stable nanoparticle composition has a release profile of buprenorphine of at least 2 months.

351. The pharmaceutical formulation of any one of clauses 262 to 341, wherein the stable nanoparticle composition has a release profile of buprenorphine of at least 3 months.

352. The pharmaceutical formulation of any one of clauses 262 to 341, wherein the release profile of the stable nanoparticle composition is a linear release profile, optionally after initial rapid release.

353. The pharmaceutical formulation of any one of clauses 262 to 341, wherein the release profile of the stable nanoparticle composition is a non-linear release profile.

354. The pharmaceutical formulation of any one of clauses 262 to 341, wherein an agent is optionally applied to the stable nanoparticle composition.

355. The pharmaceutical formulation of clause 354, wherein the agent is selected from the group consisting of a surfactant, a stabilizer, a biomarker for targeting, or a second active pharmaceutical ingredient (API).

356. The pharmaceutical formulation of any one of clauses 262 to 355, wherein the stable nanoparticle composition is administered as a single dose.

357. The pharmaceutical formulation of any one of clauses 262 to 356, wherein the stable nanoparticle composition is administered as a single unit dose.

358. The pharmaceutical formulation of any one of clauses 262 to 357, wherein the pharmaceutical formulation further comprises an additional active pharmaceutical agent.

359. A pharmaceutical formulation comprising a therapeutically effective amount of a stable nanoparticle composition, wherein the stable nanoparticle composition comprises a first nanoparticle component comprising buprenorphine and a first biodegradable polymer and a second nanoparticle component comprising buprenorphine and a second biodegradable polymer.

360. The pharmaceutical formulation of clause 359, wherein the stable nanoparticle composition further comprises a third nanoparticle component comprising buprenorphine and a third biodegradable polymer.

361. The pharmaceutical formulation of clause 359 or clause 360, wherein the stable nanoparticle composition further comprises a fourth nanoparticle component comprising buprenorphine and a fourth biodegradable polymer.

362. The pharmaceutical formulation of any one of clauses 359 to 361, wherein at least one biodegradable polymer is selected from the group consisting of polycaprolactone (PCL), polyglycolic acid (PGA), poly(DL)-lactide (PLA), poly(DL)-lactide-co-glycolide (PLGA), or mixtures thereof.

363. The pharmaceutical formulation of any one of clauses 359 to 361, wherein at least one biodegradable polymer is PLA.

364. The pharmaceutical formulation of any one of clauses 359 to 361, wherein at least one biodegradable polymer is PLGA.

365. The pharmaceutical formulation of any one of clauses 359 to 361, wherein at least one biodegradable polymer is PCL.

366. The pharmaceutical formulation of any one of clauses 359 to 361, wherein at least one biodegradable polymer is PGA.

367. The pharmaceutical formulation of any one of clauses 359 to 366, wherein the first nanoparticle component has a release profile of at least 7 days.

368. The pharmaceutical formulation of any one of clauses 359 to 366, wherein the first nanoparticle component has a release profile of at least 14 days.

369. The pharmaceutical formulation of any one of clauses 359 to 368, wherein the second nanoparticle component has a release profile of at least 7 days.

370. The pharmaceutical formulation of any one of clauses 359 to 368, wherein the second nanoparticle component has a release profile of at least 14 days.

371. The pharmaceutical formulation of any one of clauses 359 to 370, wherein the pharmaceutical formulation is a parenteral formulation.

372. The pharmaceutical formulation of clause 371, wherein the parenteral formulation is a subcutaneous parenteral formulation.

373. The pharmaceutical formulation of clause 371, wherein the parenteral formulation is an intramuscular parenteral formulation.

374. The pharmaceutical formulation of any one of clauses 359 to 373, wherein the pharmaceutical formulation is suitable for administration at a dose of about 0.001 to about 1000 mg of buprenorphine per kg of animal body weight.

375. The pharmaceutical formulation of any one of clauses 359 to 373, wherein the pharmaceutical formulation is suitable for administration at a dose of about 0.001 to about 100 mg of buprenorphine per kg of animal body weight.

376. The pharmaceutical formulation of any one of clauses 359 to 373, wherein the pharmaceutical formulation is suitable for administration at a dose of about 0.01 to about 100 mg of buprenorphine per kg of animal body weight.

377. The pharmaceutical formulation of any one of clauses 359 to 373, wherein the pharmaceutical formulation is suitable for administration at a dose of about 0.1 to about 100 mg of buprenorphine per kg of animal body weight.

378. The pharmaceutical formulation of any one of clauses 359 to 373, wherein the pharmaceutical formulation is suitable for administration at a dose of about 0.1 to about 10 mg of buprenorphine per kg of animal body weight.

379. The pharmaceutical formulation of any one of clauses 359 to 373, wherein the pharmaceutical formulation is suitable for administration at a dose of about 1 to about 5 mg of buprenorphine per kg of animal body weight.

380. The pharmaceutical formulation of any one of clauses 359 to 373, wherein the pharmaceutical formulation is suitable for administration at a dose of about 2 mg of buprenorphine per kg of animal body weight.

381. The pharmaceutical formulation of any one of clauses 359 to 373, wherein the pharmaceutical formulation is suitable for administration at a dose of about 3 mg of buprenorphine per kg of animal body weight.

382. The pharmaceutical formulation of any one of clauses 359 to 373, wherein the pharmaceutical formulation is suitable for administration at a dose of about 4 mg of buprenorphine per kg of animal body weight.

383. The pharmaceutical formulation of any one of clauses 359 to 373, wherein the pharmaceutical formulation is suitable for administration at a dose of about 5 mg of buprenorphine per kg of animal body weight.

384. The pharmaceutical formulation of any one of clauses 359 to 383, wherein the pharmaceutical formulation is which is administered once every at least one week.

385. The pharmaceutical formulation of any one of clauses 359 to 383, wherein the pharmaceutical formulation is administered once every at least two weeks.

386. The pharmaceutical formulation of any one of clauses 359 to 383, wherein the pharmaceutical formulation is administered once every at least three weeks.

387. The pharmaceutical formulation of any one of clauses 359 to 383, wherein the pharmaceutical formulation is administered once every at least four weeks.

388. The pharmaceutical formulation of any one of clauses 359 to 383, wherein the pharmaceutical formulation is administered once every at least six weeks.

389. The pharmaceutical formulation of any one of clauses 359 to 383, wherein the pharmaceutical formulation is administered once every at least two months.

390. The pharmaceutical formulation of any one of clauses 359 to 383, wherein the pharmaceutical formulation is administered once every at least three months.

391. The pharmaceutical formulation of any one of clauses 359 to 390, wherein at least one biodegradable polymer is conjugated to poly(ethylene) glycol.

392. The pharmaceutical formulation of any one of clauses 359 to 391, wherein the ratio of buprenorphine:polymer in one or more nanoparticle components is in a range between about 10:1 to about 1:50.

393. The pharmaceutical formulation of any one of clauses 359 to 391, wherein the ratio of buprenorphine:polymer in one or more nanoparticle components is in a range between about 10:1 to about 1:30.

394. The pharmaceutical formulation of any one of clauses 359 to 391, wherein the ratio of buprenorphine:polymer in one or more nanoparticle components is in a range between about 10:1 to about 1:20.

395. The pharmaceutical formulation of any one of clauses 359 to 391, wherein the ratio of buprenorphine:polymer in one or more nanoparticle components is in a range between about 10:1 to about 1:10.

396. The pharmaceutical formulation of any one of clauses 359 to 391, wherein the ratio of buprenorphine:polymer in one or more nanoparticle components is about 1.1.

397. The pharmaceutical formulation of any one of clauses 359 to 391, wherein the ratio of buprenorphine:polymer in one or more nanoparticle components is about 1:2.

398. The pharmaceutical formulation of any one of clauses 359 to 391, wherein the ratio of buprenorphine:polymer in one or more nanoparticle components is about 1:4.

399. The pharmaceutical formulation of any one of clauses 359 to 391, wherein the ratio of buprenorphine:polymer in one or more nanoparticle components is about 1:5.

400. The pharmaceutical formulation of any one of clauses 359 to 391, wherein the ratio of buprenorphine:polymer in one or more nanoparticle components is about 1:8.

401. The pharmaceutical formulation of any one of clauses 359 to 391, wherein the ratio of buprenorphine:polymer in one or more nanoparticle components is about 1:10.

402. The pharmaceutical formulation of any one of clauses 359 to 391, wherein the ratio of buprenorphine:polymer in one or more nanoparticle components is about 1:15.

403. The pharmaceutical formulation of any one of clauses 359 to 391, wherein the ratio of buprenorphine:polymer in one or more nanoparticle components is about 1:16.

404. The pharmaceutical formulation of any one of clauses 359 to 391, wherein the ratio of buprenorphine:polymer in one or more nanoparticle components is about 1:20.

405. The pharmaceutical formulation of any one of clauses 359 to 391, wherein the ratio of buprenorphine:polymer in one or more nanoparticle components is about 1:25.

406. The pharmaceutical formulation of any one of clauses 359 to 391, wherein the ratio of buprenorphine:polymer in one or more nanoparticle components is about 1:30.

407. The pharmaceutical formulation of any one of clauses 359 to 391, wherein the ratio of buprenorphine:polymer in one or more nanoparticle components is about 1:32.

408. The pharmaceutical formulation of any one of clauses 359 to 391, wherein the ratio of buprenorphine:polymer in one or more nanoparticle components is about 1:48.

409. The pharmaceutical formulation of any one of clauses 359 to 391, wherein the ratio of buprenorphine:polymer in one or more nanoparticle components is about 1:50.

410. The pharmaceutical formulation of any one of clauses 359 to 409, wherein the ratio of buprenorphine:polymer in one or more nanoparticle components wherein the stable nanoparticle composition has an average diameter from about 0.5 nm to about 1000 nm.

411. The pharmaceutical formulation of any one of clauses 359 to 409, wherein the stable nanoparticle composition has an average diameter between about 10 nm to about 500 nm.

412. The pharmaceutical formulation of any one of clauses 359 to 409, wherein the stable nanoparticle composition has an average diameter between about 100 nm to about 500 nm.

413. The pharmaceutical formulation of any one of clauses 359 to 409, wherein the stable nanoparticle composition has an average diameter between about 200 nm to about 400 nm.

414. The pharmaceutical formulation of any one of clauses 359 to 409, wherein the stable nanoparticle composition has an average diameter of about 100 nm.

415. The pharmaceutical formulation of any one of clauses 359 to 409, wherein the stable nanoparticle composition has an average diameter of about 200 nm.

416. The pharmaceutical formulation of any one of clauses 359 to 409, wherein the stable nanoparticle composition has an average diameter of about 300 nm.

417. The pharmaceutical formulation of any one of clauses 359 to 409, wherein the stable nanoparticle composition has an average diameter of about 400 nm.

418. The pharmaceutical formulation of any one of clauses 359 to 409, wherein the stable nanoparticle composition has an average diameter of about 500 nm.

419. The pharmaceutical formulation of any one of clauses 359 to 418, wherein one or more nanoparticle components further comprise one or more polymers selected from the group consisting of polyvinyl alcohol (PVA), PEG, sorbitan isostearate, sorbitan monopalmitate (Span 40), carboxymethylcellulose, poloxamer 188, polysorbate 20, polysorbate 80, or mixtures thereof.

420. The pharmaceutical formulation of any one of clauses 359 to 419, wherein the stable nanoparticle composition is lyophilized.

421. The pharmaceutical formulation of any one of clauses 359 to 420, wherein the stable nanoparticle composition has a release profile of buprenorphine of at least 24 hours.

422. The pharmaceutical formulation of any one of clauses 359 to 420, wherein the stable nanoparticle composition has a release profile of buprenorphine of at least 48 hours.

423. The pharmaceutical formulation of any one of clauses 359 to 420, wherein the stable nanoparticle composition has a release profile of buprenorphine of at least 72 hours.

424. The pharmaceutical formulation of any one of clauses 359 to 420, wherein the stable nanoparticle composition has a release profile of buprenorphine of at least 96 hours.

425. The pharmaceutical formulation of any one of clauses 359 to 420, wherein the stable nanoparticle composition has a release profile of buprenorphine of at least 7 days.

426. The pharmaceutical formulation of any one of clauses 359 to 420, wherein the stable nanoparticle composition has a release profile of buprenorphine of at least 14 days.

427. The pharmaceutical formulation of any one of clauses 359 to 420, wherein the stable nanoparticle composition has a release profile of buprenorphine of at least 21 days.

428. The pharmaceutical formulation of any one of clauses 359 to 420, wherein the stable nanoparticle composition has a release profile of buprenorphine of at least 28 days.

429. The pharmaceutical formulation of any one of clauses 359 to 420, wherein the stable nanoparticle composition has a release profile of buprenorphine of at least 2 months.

430. The pharmaceutical formulation of any one of clauses 359 to 420, wherein the stable nanoparticle composition has a release profile of buprenorphine of at least 3 months.

431. The pharmaceutical formulation of any one of clauses 359 to 420, wherein the release profile of the stable nanoparticle composition is a linear release profile, optionally after initial rapid release.

432. The pharmaceutical formulation of any one of clauses 359 to 420, wherein the release profile of the stable nanoparticle composition is a non-linear release profile.

433. The pharmaceutical formulation of any one of clauses 359 to 420, wherein an agent is optionally applied to the stable nanoparticle composition.

434. The pharmaceutical formulation of clause 433, wherein the agent is selected from the group consisting of a surfactant, a stabilizer, a biomarker for targeting, or a second active pharmaceutical ingredient (API).

435. The pharmaceutical formulation of any one of clauses 359 to 434, wherein the stable nanoparticle composition is administered as a single dose.

436. The pharmaceutical formulation of any one of clauses 359 to 435, wherein the stable nanoparticle composition is administered as a single unit dose.

437. The pharmaceutical formulation of any one of clauses 359 to 436, wherein the pharmaceutical formulation further comprises an additional active pharmaceutical agent.

Figure 1:
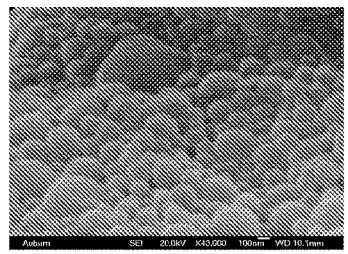
FIG. 1 shows the morphology of buprenorphine/PLGA nanoparticles (Formula B (drug:polymer ratio of 1:16)).

Various embodiments of the invention are described herein as follows. In one embodiment described herein, a stable nanoparticle composition is provided. The stable nanoparticle composition comprises buprenorphine and at least one biodegradable polymer.

In another embodiment, a method of controlling pain in an animal is provided. The method comprises administering to the animal in need thereof a therapeutically effective amount of a stable nanoparticle composition comprising buprenorphine and at least one biodegradable polymer.

In yet another embodiment, a method of treating addiction in a human is provided. The method comprises administering to the animal in need thereof a therapeutically effective amount of a stable nanoparticle composition comprising buprenorphine and at least one biodegradable polymer.

In another embodiment, a pharmaceutical formulation is provided. The pharmaceutical formulation comprises a therapeutically effective amount of a stable nanoparticle composition, wherein the composition comprises buprenorphine and at least one biodegradable polymer.

In yet another embodiment, another pharmaceutical formulation is provided. The pharmaceutical formulation comprises a therapeutically effective amount of a stable nanoparticle composition, wherein the composition comprises a first nanoparticle component comprising buprenorphine and a first biodegradable polymer and a second nanoparticle component comprising buprenorphine and a second biodegradable polymer.

In the various embodiments, the stable nanoparticle composition comprises buprenorphine and at least one biodegradable polymer. The term "stable," when applied to nanoparticle compositions disclosed herein, means that the compositions maintain one or more aspects of their physical structure (e.g., size range, distribution of particles, and/or percentage of active pharmaceutical ingredient (API)) over a period of time. In some embodiments of the invention, a stable nanoparticle composition is one for which the average particle size, the maximum particle size, the range of particle sizes, and/or the distribution of particle sizes (i.e., the percentage of particles above a designated size and/or outside a designated range of sizes) is maintained for a period of time. In some embodiments, the period of time is at least about one (1) day, about one (1) week, about two (2) weeks, about one (1) month, about two (2) months, about three (3) months, about four (4) months, about five (5) months, about six (6) months, about eight (8) months, about ten (10) months, about twelve (12) months, about twenty-four (24) months, or longer. In some embodiments, the period of time is within the range of about one (1) day to about twenty-four (24) months, about two (2) weeks to about twelve (12) months, about two (2) months to about five (5) months, etc. For example, if a nanoparticle composition is subjected to prolonged storage, temperature changes, and/or pH changes and a majority of the nanoparticles in the population maintain a diameter within a stated range, the nanoparticle composition is stable. For some such populations, a majority is more than about 50%, about 60%, about 70%, about 80%, about 90%, about 95%, about 96%, about 97%, about 98%, about 99%, about 99.5%, about 99.6%, about 99.7%, about 99.8%, about 99.9%, or more. In some embodiments, a "stable" nanoparticle composition is one for which a specified percentage of active pharmaceutical ingredient (API) remains in the nanoparticle composition. In some embodiments, the percentage of API is at least about 70%, about 75%, about 80%, about 85%, about 90%, about 95%, about 96%, about 97%, about 98%, about 99%, about 99.5%, about 99.6%, about 99.7%, about 99.8%, about 99.9%, or more. In one embodiment, the percentage of API is at least about 90%.

The term "nanoparticle" refers to a particle having a size measured on the nanometer scale. As used herein, the "nanoparticle" refers to a particle having a structure with a size of less than about 1,000 nanometers. As used herein, the term "nanoparticle composition" refers to any substance that contains at least one nanoparticle. In some embodiments, a nanoparticle composition is a uniform collection of nanoparticles.

In the various embodiments, the stable nanoparticle composition comprises buprenorphine. Buprenorphine is a partial μ-opioid receptor agonist and is also known by chemical names such (2S)-2-[(5R,6R,7R,14S)-9α-Cyclopropylmethyl-4,5-epoxy-6,14-ethano-3-hydroxy-6-methoxymorphinan-7-yl]-3,3-dimethylbutan-2-ol. The chemical structure of buprenorphine is:

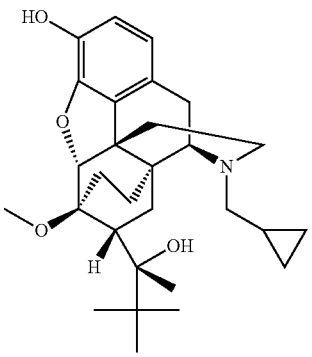 [SMILES: CO[C@@]12CC[C@@]3(C[C@@H]1[C@](C)(O)C(C)(C)C)[C@H]1Cc4ccc(O)c5c4[C@@]3(CCN1CC1CC1)[C@H]2O5]

As used herein, the term "buprenorphine" refers to buprenorphine base, pharmaceutically acceptable salts of buprenorphine, other salts of buprenorphine, metabolites of buprenorphine (e.g., norbuprenorphine), and prodrugs of buprenorphine. The term "pharmaceutically acceptable salt" refers to an addition salt that exists in conjunction with the acidic or basic portion of buprenorphine. Such salts include the pharmaceutically acceptable salts listed in HANDBOOK OF PHARMACEUTICAL SALTS: PROPERTIES, SELECTION AND USE, P. H. Stahl and C. G. Wermuth (Eds.), Wiley-VCH, New York, 2002 which are known to the skilled artisan. Pharmaceutically acceptable salts of an acid addition nature are formed when buprenorphine and any of its intermediates containing a basic functionality are reacted with a pharmaceutically acceptable acid. Pharmaceutically acceptable acids commonly employed to form such acid addition salts include inorganic and organic acids. Pharmaceutically acceptable salts of a base addition nature are formed when buprenorphine and any of its intermediates containing an acidic functionality are reacted with a pharmaceutically acceptable base. Pharmaceutically acceptable bases commonly employed to form base addition salts include organic and inorganic bases.

In addition to pharmaceutically acceptable salts, other salts are included in the present invention. They may serve as intermediates in the purification of compounds or in the preparation of other pharmaceutically-acceptable salts, or are useful for identification, characterization or purification.

In one embodiment, buprenorphine refers to a metabolite of buprenorphine. Metabolites of buprenorphine are known in the art, for example, norbuprenorphine. In another embodiment, buprenorphine refers to a prodrug of buprenorphine. Prodrugs of buprenorphine are known in the art.

In the various embodiments, the stable nanoparticle composition comprises at least one biodegradable polymer. As used herein, the term "biodegradable" refers to a material that gradually decomposes, dissolves, hydrolyzes and/or erodes. Generally, the "biodegradable polymers" herein are polymers that are hydrolysable, and/or bioerodable in-situ primarily through hydrolysis and/or enzymolysis. The term "biodegradable polymer" as used herein is meant to include any biocompatible and/or biodegradable synthetic and natural polymers that can be used in vivo.

In some embodiments, the biodegradable polymer is selected from the group consisting of polycaprolactone (PCL), polyglycolic acid (PGA), poly(DL)-lactide (PLA), poly(DL)-lactide-co-glycolide (PLGA), or mixtures thereof. In one embodiment, the biodegradable polymer is PLA. In another embodiment, the biodegradable polymer is PLGA.

In yet another embodiment, the biodegradable polymer is PCL. In one embodiment, the biodegradable polymer is PGA.

In various embodiments, the stable nanoparticle composition comprises more than one biodegradable polymer. In some embodiments, the stable nanoparticle composition comprises two biodegradable polymers. In one embodiment, the ratio of the first biodegradable polymer to the second biodegradable polymer is in a range between about 1:99 to about 99:1. In another embodiment, the ratio of the first biodegradable polymer to the second biodegradable polymer is in a range between about 5:95 to about 95:5. In yet another embodiment, the ratio of the first biodegradable polymer to the second biodegradable polymer is in a range between about 10:90 to about 90:10. In one embodiment, the ratio of the first biodegradable polymer to the second biodegradable polymer is in a range between about 15:85 to about 85:15. In another embodiment, the ratio of the first biodegradable polymer to the second biodegradable polymer is in a range between about 20:80 to about 80:20. In yet another embodiment, the ratio of the first biodegradable polymer to the second biodegradable polymer is in a range between about 25:75 to about 75:25. In one embodiment, the ratio of the first biodegradable polymer to the second biodegradable polymer is in a range between about 30:70 to about 70:30. In another embodiment, the ratio of the first biodegradable polymer to the second biodegradable polymer is in a range between about 35:65 to about 65:35. In yet another embodiment, the ratio of the first biodegradable polymer to the second biodegradable polymer is in a range between about 40:60 to about 60:40. In another embodiment, the ratio of the first biodegradable polymer to the second biodegradable polymer is in a range between about 45:55 to about 55:45.

In one embodiment, the ratio of the first biodegradable polymer to the second biodegradable polymer is about 10:90. In another embodiment, the ratio of the first biodegradable polymer to the second biodegradable polymer is about 15:85. In yet another embodiment, the ratio of the first biodegradable polymer to the second biodegradable polymer is about 25:75. In one embodiment, the ratio of the first biodegradable polymer to the second biodegradable polymer is about 50:50. In another embodiment, the ratio of the first biodegradable polymer to the second biodegradable polymer is about 75:25. In yet another embodiment, the ratio of the first biodegradable polymer to the second biodegradable polymer is about 85:15. In yet another embodiment, the ratio of the first biodegradable polymer to the second biodegradable polymer is about 90:10.

In various aspects, the stable nanoparticle composition comprises more than one biodegradable polymer. In one embodiment, one biodegradable polymer is PLA. In another embodiment, one biodegradable polymer is PLGA. In yet another embodiment, one biodegradable polymer is PCL. In another embodiment, one biodegradable polymer is PGA.

In other aspects, the stable nanoparticle composition comprises two biodegradable polymers. In one embodiment, the first biodegradable polymer is PLA and the second biodegradable polymer is PLGA.

In other aspects, at least one biodegradable polymer of the stable nanoparticle composition is conjugated to poly(ethylene) glycol. As used herein, the term "conjugated" refers to a complex formed between at least one nanoparticle and at least one additional agent. For example, at least one nanoparticle can be conjugated to a poly(ethylene) glycol (PEG) of varying molecular weights as known in the art. In some embodiments, the PEG may have an average molecular weight of about, e.g., 500, 1000, 2000, 3000, 3350, 3500, 4000, 4500, 5000, 6000, 8000, 10,000, or 100,000 Daltons (Da), or an average molecular weight ranging from, e.g., about 100 Da to about 100,000 Da, about 100 Da to about 6,000 Da, about 500 Da to about 5000 Da, about 1000 Da to about 4000 Da, about 2000 Da to about 4000 Da, about 2000 Da to about 6000 Da, about 1000 Da to about 10,000 Da, or about 3000 Da to about 4000 Da.

In various embodiments, the stable nanoparticle composition can have a specified ratio of buprenorphine:polymer. In one embodiment, the ratio of buprenorphine:polymer is in a range between about 10:1 to about 1:50. In another embodiment, the ratio of buprenorphine:polymer is in a range between about 10:1 to about 1:30. In yet another embodiment, the ratio of buprenorphine:polymer is in a range between about 10:1 to about 1:20. In another embodiment, the ratio of buprenorphine:polymer is in a range between about 10:1 to about 1:10.

In one embodiment, the ratio of buprenorphine:polymer is about 1:1. In another embodiment, the ratio of buprenorphine:polymer is about 1:2. In yet another embodiment, the ratio of buprenorphine:polymer is about 1:4. In one embodiment, the ratio of buprenorphine:polymer is about 1:5. In another embodiment, the ratio of buprenorphine:polymer is about 1:8. In yet another embodiment, the ratio of buprenorphine:polymer is about 1:10. In one embodiment, the ratio of buprenorphine:polymer is about 1:15. In another embodiment, the ratio of buprenorphine:polymer is about 1:16. In yet another embodiment, the ratio of buprenorphine:polymer is about 1:20. In one embodiment, the ratio of buprenorphine:polymer is about 1:25. In another embodiment, the ratio of buprenorphine:polymer is about 1:30. In yet another embodiment, the ratio of buprenorphine:polymer is about 1:32. In another embodiment, the ratio of buprenorphine:polymer is about 1:48. In yet another embodiment, the ratio of buprenorphine:polymer is about 1:50.

In various embodiments, the stable nanoparticle composition can have a specified amount of buprenorphine present in the composition. In one embodiment, the amount of buprenorphine is present at a range between about 0.001 to about 1000 mg. In another embodiment, the amount of buprenorphine is present at a range between about 0.001 to about 100 mg. In yet another embodiment, the amount of buprenorphine is present at a range between about 0.1 to about 100 mg.

In various aspects, the stable nanoparticle composition can have a specified diameter. In one embodiment, the stable nanoparticle composition has a diameter from about 0.5 nm to about 1000 nm. In another embodiment, the stable nanoparticle composition has a diameter between about 10 nm to about 500 nm. In yet another embodiment, the stable nanoparticle composition has a diameter between about 100 nm to about 500 nm. In another embodiment, the stable nanoparticle composition has a diameter between about 200 nm to about 400 nm.

In one embodiment, the stable nanoparticle composition has a diameter of about 100 nm. In another embodiment, the stable nanoparticle composition has a diameter of about 200 nm. In yet another embodiment, the stable nanoparticle composition has a diameter of about 300 nm. In another embodiment, the stable nanoparticle composition has a diameter of about 400 nm. In yet another embodiment, the stable nanoparticle composition has a diameter of about 500 nm.

In various embodiments, the stable nanoparticle composition further comprises one or more polymers. In one aspect, the stable nanoparticle composition further comprises one or more polymers selected from the group consisting of polyvinyl alcohol (PVA), PEG, sorbitan isostearate, sorbitan monopalmitate (Span 40), carboxymethylcellulose, poloxamer 188, polysorbate 20, polysorbate 80, or mixtures thereof.

In various embodiments, the stable nanoparticle composition is lyophilized. The stable nanoparticle compositions according to the present disclosure can be lyophilized to produce lyophilisates by conventional lyophilization or powders. The term "lyophilization," also known as freeze-drying, is a commonly employed technique to remove water from the preparation of interest. Lyophilization is a process by which the material to be dried is first frozen and then the ice or frozen solvent is removed by sublimation in a vacuum environment. An excipient may be included in pre-lyophilized formulations to enhance stability during the freeze-drying process and/or to improve stability of the lyophilized product upon storage. For example, see Pikal, M. Biopharm. 3(9)26-30 (1990) and Arakawa et al. Pharm. Res. 8(3):285-291 (1991).

The stable nanoparticle compositions according to the present disclosure can also be dried prior to storage and/or sterilization using other methods known in the art. For example, the stable nanoparticle compositions can be air (e.g., low heat) dried, spray dried, or any other drying method known in the art. Spray drying of compositions pharmaceutical ingredients is known to those of ordinary skill in the art. For example, see Broadhead, J. et al., "The Spray Drying of Pharmaceuticals," in Drug Dev. Ind. Pharm. 18 (11 & 12), 1169-1206 (1992). Spray drying is a useful technique because it can convert a pharmaceutical preparation into a fine, dustless or agglomerated powder in a one-step process. The basic technique comprises the following four steps: a) atomization of the feed solution into a spray; b) spray-air contact; c) drying of the spray; and d) separation of the dried product from the drying air. For example, U.S. Pat. Nos. 6,235,710 and 6,001,800 describe the preparation of drug by spray drying.

In various aspects, the stable nanoparticle composition has a specified release profile. As used herein, the term "release profile" refers to the rate at which buprenorphine is released from the nanoparticle composition (e.g., the rate that the nanoparticle composition releases an amount of buprenorphine). In one embodiment, the stable nanoparticle composition has a release profile of buprenorphine of at least 24 hours. In another embodiment, the stable nanoparticle composition has a release profile of buprenorphine of at least 48 hours. In yet another embodiment, the stable nanoparticle composition has a release profile of buprenorphine of at least 72 hours. In one embodiment, the stable nanoparticle composition has a release profile of buprenorphine of at least 96 hours. In another embodiment, the stable nanoparticle composition has a release profile of buprenorphine of at least 7 days. In yet another embodiment, the stable nanoparticle composition has a release profile of buprenorphine of at least 14 days. In one embodiment, the stable nanoparticle composition has a release profile of buprenorphine of at least 21 days. In another embodiment, the stable nanoparticle composition has a release profile of buprenorphine of at least 28 days. In yet another embodiment, the stable nanoparticle composition has a release profile of buprenorphine of at least 2 months. In another embodiment, the stable nanoparticle composition has a release profile of buprenorphine of at least 3 months.

In various aspects, the stable nanoparticle composition has a linear release profile. The term "linear release" or "linear release profile" as used herein means a constant, linear, continuous, sustained and controlled release rate of buprenorphine nanoparticle composition, i.e. the plot of drug vs. time is linear. In some embodiments, the stable nanoparticle composition has a linear release profile after initial rapid release. In other embodiments, the release profile of the stable nanoparticle composition is a non-linear release profile.

In various embodiments, an agent is optionally applied to the stable nanoparticle composition. In one aspect, the agent is selected from the group consisting of a surfactant, a stabilizer, a biomarker for targeting, or a second active pharmaceutical ingredient (API). The term "surfactant," as used herein, is to be interpreted broadly to relate to any composition that is capable of altering "surface tension between a liquid and any precipitated particles suspended in the liquid. Suitable surfactants are taught in McCutcheon's Emulsifiers & Detergents, at pages 287-310 of the North American Edition (1994), and in McCutcheon's Emulsifiers & Detergents, at pages 257-278 and 280 of the International Edition (1994), both published by MC Publishing Co. (McCutcheon Division) of Glen Rock, N.J.

As used herein, the term "stabilizer" refers to any chemical, compound, or material that minimizes the degradation of buprenorphine or biodegradable polymer in the nanoparticle compositions. Examples of stabilizers include, but are not limited to, aluminum salts, bicarbonate salts of aluminum, Group IA metals or Group IIA metal salts (such as, but not limited to, sodium salts, calcium salts, magnesium salts, etc.), bicarbonate salts of Group IA or Group IIA salts (such as a bicarbonate salt of sodium, a bicarbonate salt of magnesium, a bicarbonate salt of calcium), polymers, sodium alginate, sterols, fatty alcohols and combinations thereof. Examples of polymers that can be used as stabilizers include, but are not limited to, semipermeable homopolymers, semipermeable copolymers, and the like.

As used herein, a "biomarker" for targeting includes any such biomarkers known in the art to be capable of targeting cells and/or disease processes. For example, a biomarker of a disease or condition refers to a gene or a gene product that is up- or down-regulated in a biological sample of a subject having the disease or condition relative to a biological sample from like tissue derivation, which gene or gene product is sufficiently specific to the disease or condition that it can be used, optionally with other genes or gene products, to identify or detect the disease or condition.

In various embodiments, stable nanoparticle composition is adapted for use as a parenteral formulation. The term "parenteral formulation" refers to a formulation suitable for the administration of the stable nanoparticle composition via injection under or through one or more layers of skin or mucus membranes of an animal, such as a human. Standard parenteral injections are given into the intradermal, subcutaneous, or intramuscular region of an animal. In some embodiments, a deep location is targeted for injection of the stable nanoparticle compositions as described herein. In one embodiment, the parenteral formulation is a subcutaneous parenteral formulation. In another embodiment, the parenteral formulation is an intramuscular parenteral formulation.

In another aspect of the present disclosure, a method of controlling pain in an animal is provided. The method comprises administering to the animal in need thereof a therapeutically effective amount of a stable nanoparticle composition comprising buprenorphine and at least one biodegradable polymer. The previously described embodiments of the stable nanoparticle composition are applicable to the method of controlling pain in an animal described herein.

As used herein, the terms "control of pain" or "controlling pain" refer to preventing, minimizing, or eliminating pain in an animal. As used herein, the term "pain" represents all categories of pain, including traumatic pain resulting from tissue injury, post-surgical pain, burn pain, inflammatory pain, pain associated with disease (such as cancer, infection, osteoarthritis, rheumatoid arthritis, or other type of arthritis), pain associated with nerve damage, neuropathy, and other forms of neuralgic, neuropathic and idiopathic pain syndromes, and specific organ or tissue pain, such as ocular and corneal pain, bone pain, heart pain, skin pain, visceral (kidney, gall bladder, gastrointestinal, etc.) pain, joint pain, dental pain, and muscle pain. The term "pain" also includes pain of varying severity, i.e. mild, moderate and severe pain, as well as acute and chronic pain.

In various embodiments of the method, the pain is associated with a surgery performed or to be performed on the animal. In another embodiment, the pain is acute pain. The term "acute pain" refers to pain resulting from an acute event and generally decreasing in intensity over a period of a few days to a few weeks. In yet another embodiment, the pain is chronic pain. The term "chronic pain" refers to pain resulting from an acute or repeated events and generally increasing in intensity over a period of a few weeks to years.

As used herein, the term "animal" refers to a mammal, for example, a human or a non-human mammal, e.g., a primate, dog, cat, bovine, ovine, porcine, equine, mouse, rat, hamster, rabbit, or guinea pig. The terms "patient," "subject," or "individual" can be used interchangeably to refer to an animal. In one embodiment, the animal is a human. In another embodiment, the animal is an equine.

In carrying out the methods of this disclosure, the amount of buprenorphine in the stable nanoparticle composition is adequate to achieve a therapeutic effect. As used herein, the term "therapeutically effective amount" refers to an amount which gives the desired benefit to an animal and includes both treatment and prophylactic administration. The amount will vary from one animal to another and will depend upon a number of factors, including the overall physical condition of the animal and the underlying cause of the condition to be treated.

The amount of buprenorphine used for the controlling pain gives an acceptable rate of change and maintains desired response at a beneficial level. A therapeutically effective amount of the composition used in the methods of the present disclosure may be readily ascertained by one of ordinary skill in the art using publicly available materials and procedures. In one embodiment of the present invention, the therapeutically effective amount of buprenorphine to be delivered can be quantified by determining milligrams of buprenorphine per kilogram of animal body weight.

In various aspects of the method, the therapeutically effective amount is an amount sufficient to achieve a minimum effective plasma concentration (MEC). Generally, MEC has been defined as the minimum plasma concentration of an analgesic that is sufficient to prevent a patient from requesting a supplementary analgesic. The MEC of buprenorphine is well known to the skilled artisan.

In some embodiments of the method, the therapeutically effective amount of buprenorphine in the stable nanoparticle composition is administered to the animal at a dose of about 0.001 to about 1000 mg of buprenorphine per kg of animal body weight. In one embodiment, the therapeutically effective amount of buprenorphine in the stable nanoparticle composition is administered to the animal at a dose of about 0.001 to about 100 mg of buprenorphine per kg of animal body weight. In another embodiment, the therapeutically effective amount of buprenorphine in the stable nanoparticle composition is administered to the animal at a dose of about 0.01 to about 100 mg of buprenorphine per kg of animal body weight. In yet another embodiment, the therapeutically effective amount of buprenorphine in the stable nanoparticle composition is administered to the animal at a dose of about 0.1 to about 100 mg of buprenorphine per kg of animal body weight. In one embodiment, the therapeutically effective amount of buprenorphine in the stable nanoparticle composition is administered to the animal at a dose of about 0.1 to about 10 mg of buprenorphine per kg of animal body weight. In another embodiment, the therapeutically effective amount of buprenorphine in the stable nanoparticle composition is administered to the animal at a dose of about 1 to about 5 mg of buprenorphine per kg of animal body weight.

In one embodiment, the therapeutically effective amount of buprenorphine in the stable nanoparticle composition is administered to the animal at a dose of about 1 mg of buprenorphine per kg of animal body weight. In another embodiment, the therapeutically effective amount of buprenorphine in the stable nanoparticle composition is administered to the animal at a dose of about 2 mg of buprenorphine per kg of animal body weight. In yet another embodiment, the therapeutically effective amount of buprenorphine in the stable nanoparticle composition is administered to the animal at a dose of about 3 mg of buprenorphine per kg of animal body weight. In another embodiment, the therapeutically effective amount of buprenorphine in the stable nanoparticle composition is administered to the animal at a dose of about 4 mg of buprenorphine per kg of animal body weight. In yet another embodiment, the therapeutically effective amount of buprenorphine in the stable nanoparticle composition is administered to the animal at a dose of about 5 mg of buprenorphine per kg of animal body weight.

In various aspects of the method, the stable nanoparticle composition is administered as a single dose. In other aspects of the method, the stable nanoparticle composition is administered as a single unit dose. As used herein, the term "unit dose" is a discrete amount of the composition comprising a predetermined amount of buprenorphine. The amount of buprenorphine is generally equal to the dosage of buprenorphine which would be administered to an animal or a convenient fraction of such a dosage such as, for example, one-half or one-third of such a dosage.

According to the methods of the present disclosure, the terms "single dose" and "single unit dose" include embodiments wherein the composition can be administered as a single parenteral injection or administered as multiple parenteral injections. In one embodiment, a single dose or single unit dose of the composition can be parenterally administered to an animal at one location on the animal's body. In another embodiment, a single dose or single unit dose of the composition can be parenterally administered to an animal in multiple injections at a single location on the animal's body. In yet another embodiment, a single dose or single unit dose of the composition can be parenterally administered to an animal in multiple injections at more than one location on the animal's body. In embodiments wherein multiple injections of the composition are utilized, the multiple injections can be administered to the animal over a reasonable duration of time.

In another aspect of the present disclosure, a method of treating addiction in a human is provided. The method comprises administering to the animal in need thereof a therapeutically effective amount of a stable nanoparticle composition comprising buprenorphine and at least one biodegradable polymer. The previously described embodiments of the stable nanoparticle composition are applicable to the method of treating addiction in a human described herein. The previously described embodiments of the method of controlling pain in an animal, with respect to animals, the amount of buprenorphine in the stable nanoparticle composition is adequate to achieve a therapeutic effect, the therapeutically effective amount of buprenorphine in the stable nanoparticle composition administered to the animal, single doses, and single unit doses are also applicable to the method of treating addiction in a human.

As used herein, the term "addiction" broadly encompasses the process whereby physical and/or psychological dependence develops to a drug. The withdrawal symptoms can reinforce the addiction, driving the user to continue taking the drug. Drug addiction is considered a pathological state. The disorder of addiction involves the progression of acute drug use to the development of drug-seeking behavior, the vulnerability to relapse, and the decreased, slowed ability to respond to naturally rewarding stimuli. The Diagnostic and Statistical Manual of Mental Disorders, Fourth Edition (DSM-IV) has categorized three stages of addiction: preoccupation/anticipation, binge/intoxication, and withdrawal/negative affect. These stages are characterized, respectively, by constant cravings and preoccupation with obtaining the substance; using more of the substance than necessary to experience the intoxicating effects; and experiencing tolerance, withdrawal symptoms, and decreased motivation for normal life activities. The term "drug addiction" as used herein is a state of periodic or chronic intoxication produced by the repeated consumption of a drug (natural or synthetic). Its characteristics include: (i) an overpowering desire or need (compulsion) to continue taking the drug and to obtain it by any means; (ii) a tendency to increase the dose; (iii) a psychic (psychological) and generally a physical dependence on the effects of the drug; and (iv) detrimental effects on the individual and on society. In one embodiment, the addiction is an opiate addiction.

In another aspect of the present disclosure, a pharmaceutical formulation is provided. The pharmaceutical formulation comprises a therapeutically effective amount of a stable nanoparticle composition, wherein the composition comprises buprenorphine and at least one biodegradable polymer. The previously described embodiments of the stable nanoparticle composition are applicable to the pharmaceutical formulation.

In various embodiments, the pharmaceutical formulation is suitable for administration at a specified dose range. In one embodiment, pharmaceutical formulation is suitable for administration at a dose of about 0.001 to about 1000 mg of buprenorphine per kg of animal body weight. In another embodiment, the pharmaceutical formulation is suitable for administration at a dose of about 0.001 to about 100 mg of buprenorphine per kg of animal body weight. In yet another embodiment, the pharmaceutical formulation is suitable for administration at a dose of about 0.01 to about 100 mg of buprenorphine per kg of animal body weight. In one embodiment, the pharmaceutical formulation is suitable for administration at a dose of about 0.1 to about 100 mg of buprenorphine per kg of animal body weight. In another embodiment, the pharmaceutical formulation is suitable for administration at a dose of about 0.1 to about 10 mg of buprenorphine per kg of animal body weight. In yet another embodiment, the pharmaceutical formulation is suitable for administration at a dose of about 1 to about 5 mg of buprenorphine per kg of animal body weight. In one embodiment, the pharmaceutical formulation is suitable for administration at a dose of about 2 mg of buprenorphine per kg of animal body weight. In another embodiment, the pharmaceutical formulation is suitable for administration at a dose of about 3 mg of buprenorphine per kg of animal body weight. In yet another embodiment, the pharmaceutical formulation is suitable for administration at a dose of about 4 mg of buprenorphine per kg of animal body weight. In another embodiment, the pharmaceutical formulation is suitable for administration at a dose of about 5 mg of buprenorphine per kg of animal body weight.

In various aspects, the pharmaceutical formulation is administered at specified time intervals. In one embodiment, the pharmaceutical formulation is administered once every at least one week. In another embodiment, the pharmaceutical formulation is administered once every at least two weeks. In yet another embodiment, the pharmaceutical formulation is administered once every at least three weeks. In one embodiment, the pharmaceutical formulation is administered once every at least four weeks. In another embodiment, the pharmaceutical formulation is administered once every at least six weeks. In yet another embodiment, the pharmaceutical formulation is administered once every at least two months. In another embodiment, the pharmaceutical formulation is administered once every at least three months.

In other embodiments, the pharmaceutical formulation further comprises an additional active pharmaceutical agent.

In another aspect of the present disclosure, a second pharmaceutical formulation is provided. The pharmaceutical formulation comprises a therapeutically effective amount of a stable nanoparticle composition, wherein the composition comprises a first nanoparticle component comprising buprenorphine and a first biodegradable polymer and a second nanoparticle component comprising buprenorphine and a second biodegradable polymer. The previously described embodiments of the first described pharmaceutical formulation are applicable to the second pharmaceutical formulation.

In some embodiments of this pharmaceutical formulation, the stable nanoparticle composition further comprises a third nanoparticle component comprising buprenorphine and a third biodegradable polymer. In other embodiments of this pharmaceutical formulation, the stable nanoparticle composition further comprises a fourth nanoparticle component comprising buprenorphine and a fourth biodegradable polymer.

In various embodiments of this pharmaceutical formulation, the first nanoparticle component of the pharmaceutical formulation has a release profile of at least 7 days. In other embodiments of this pharmaceutical formulation, the first nanoparticle component has a release profile of at least 14 days. In yet other embodiments of this pharmaceutical formulation, the second nanoparticle component has a release profile of at least 7 days. In still other embodiments of this pharmaceutical formulation, the second nanoparticle component has a release profile of at least 14 days.

EXAMPLE 1

Preparation of Stable Nanoparticle Compositions

The stable nanoparticle compositions comprise buprenorphine and at least one biodegradable polymer. In this example, the nanoparticle compositions can be prepared from poly(DL)-lactide-co-glycolide (PLGA) or poly(DL)-lactide (PLA).

1. Buprenorphine/PLGA Nanoparticles

Buprenorphine/PLGA nanoparticles can be prepared, for example, as follows. Buprenorphine hydrochloride was purchased from Sigma (St. Louis, Mo.). PLGA (ratio 50:50) was purchase from Lactel Absorbable Polymer (Pelham, Ala.). Polyvinyl alcohol (PVA) and phosphate buffered saline (PBS) pH 7.4 were purchased from Sigma (St. Louis, Mo.). Hydrochloric acid, sodium bicarbonate, potassium phosphate, sodium phosphate, acetonitrile, sodium lauryl sulfate, acetone, and methylene chloride were obtained from Fisher (Fair Lawn, N.J.).

Buprenorphine hydrochloride was converted to buprenorphine free base by adding saturated sodium bicarbonate solution into the buprenorphine aqueous solution to precipitate the base. The precipitate was filtered with a vacuum filter and placed under a hood to dry.

Buprenorphine base and PLGA were dissolved in 2.5 mL methylene chloride with at a ratio of drug:polymer ratio of either 1:16 (Formula A or Formula B) or 1:8 (Formula C). The organic mixture was added into a 10 mL 1% PVA solution and homogenized about 15 pulses at 70% power. This emulsion was then transferred to a beaker with 50 mL 0.1% PVA solution with continued stirring by a magnetic stirrer for another 4 hours (Formula A) or 24 hours (Formulas B and C).

The mixture was then centrifuged at 10,000 rpm for 10 minutes and the upper layer was decanted. The nanoparticles were washed with de-ionized water and centrifuged again. The final product was frozen at −80° C. and lyophilized. The nanoparticle compositions were stored in a freezer for further analyses.

2. Buprenorphine/PLA Nanoparticles

Buprenorphine/PLA nanoparticles can be prepared, for example, as follows. Buprenorphine base was a gift from Noramco Inc. (Wilmington, Del.). PLA and phosphate buffered saline (PBS) pH 7.4 were purchased from Lactel Absorbable Polymer (Pelham, Ala.). Polyvinyl alcohol (PVA) was purchased from Sigma (St. Louis, Mo.). Potassium phosphate, sodium phosphate, acetonitrile, sodium lauryl sulfate, and ethyl acetate were obtained from Fisher (Fair Lawn, N.J.).

Buprenorphine base and PLA were dissolved in 2.5 mL ethyl acetate with drug:polymer ratio 1:16 (Formula B) or 1:8 (Formula C). The organic mixture was added into a 10 mL 1% PVA solution and homogenized about 1 minute at 70% power. This emulsion was then transferred to a flask with 50 mL 0.05% PVA solution and continuously stirred with a magnetic stirrer for another 24 hours (Formulas B and C). The final product was frozen at −80° C. and lyophilized. The nanoparticle compositions were stored in a freezer for further analyses.

EXAMPLE 2

Morphological Evaluation of Stable Nanoparticle Compositions

The morphology of nanoparticle compositions can be analyzed by scanning electron microscopy (SEM). In this example, buprenorphine/PLGA nanoparticle compositions were evaluated.

Figure 2:
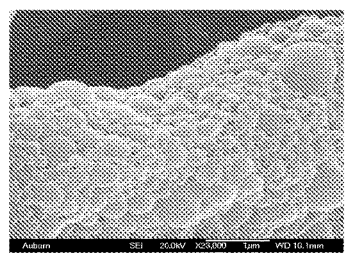
FIG. 2 shows the morphology of buprenorphine/PLGA nanoparticles (Formula C (drug:polymer ratio of 1:8)).

FIG. 1 shows the morphology of buprenorphine/PLGA nanoparticles (Formula B (drug:polymer ratio of 1:16)). FIG. 2 shows the morphology of buprenorphine/PLGA nanoparticles (Formula C (drug:polymer ratio of 1:8)). As shown in FIGS. 1 and 2, the morphology of the buprenorphine/PLGA nanoparticles demonstrated their nanosphere shape, and did not show cylindrical or needle-like particles.

EXAMPLE 3

X-Ray Diffraction Evaluation of Stable Nanoparticle Compositions

The nanoparticle compositions can be analyzed via X-ray diffraction to evaluate the dispersion of buprenorphine. In this example, buprenorphine/PLA nanoparticle compositions were evaluated.

Figure 3:
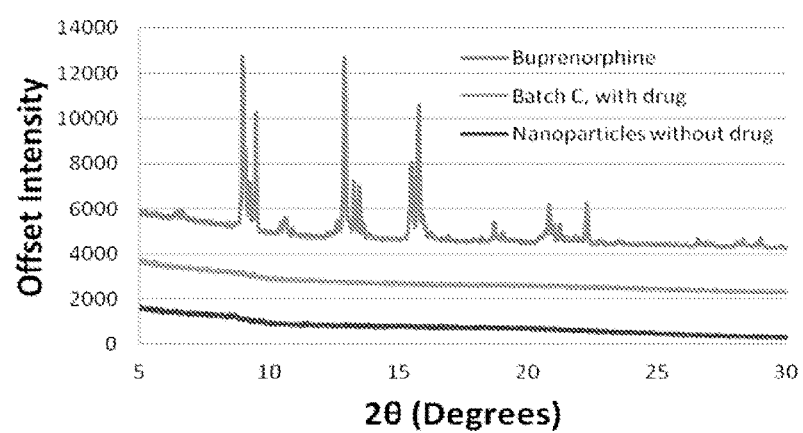
FIG. 3 shows the results of the X-ray diffraction evaluation of buprenorphine/PLA nanoparticles. The evaluated samples were a) buprenorphine alone (top line), b) buprenorphine/PLA nanoparticles (Formula C (drug:polymer ratio 1:8)) (middle line) and c) mock nanoparticles (bottom line).

A D8 Discover and Bruker AXS GmbH (Bruker, Karlshuhe, Germany) were utilized to analyze the presence of crystalline forms in various samples. The evaluated samples included a) buprenorphine alone, b) buprenorphine/PLA nanoparticles (Formula C (drug:polymer ratio 1:8)) and c) mock nanoparticles (i.e., without buprenorphine). FIG. 3 shows the results of the X-ray diffraction evaluation. As demonstrated in FIG. 3, buprenorphine is present inside the buprenorphine/PLA nanoparticles as a non-crystalline dispersion (matrix system).

EXAMPLE 4

Loading Efficiency of Buprenorphine/PLGA Nanoparticle Compositions

The loading efficiency of buprenorphine in the nanoparticle compositions can be analyzed. In this example, buprenorphine/PLGA nanoparticle compositions were evaluated.

The loading efficiency of buprenorphine/PLGA nanoparticle compositions was analyzed by high performance liquid chromatography (HPLC). Three different buprenorphine/PLGA nanoparticle samples were evaluated: Formula A (drug:polymer ratio 1:16), Formula B (drug:polymer ratio 1:16), and Formula C (drug:polymer ratio 1:8).

The HPLC system was composed of a reverse phase C-18 column (Phenomenex, Torrance, Calif.) with a UV detector (wavelength: 210 nm). The mobile phase was composed of 80% acetonitrile and 20% phosphate buffer (pH 6) and the flow rate was 1 ml/min. Two milligrams (mg) of buprenorphine/PLGA nanoparticles were dissolved in 1 ml of HPLC-grade acetone. A 20 µl aliquot of the solution was mixed with 250 µl of mobile phase and injected into the HPLC. Drug concentrations and amount were based on a standard curve. Each formulation of nanoparticles was analyzed in triplicate. Results are shown in Table 1. Compared with Formulas B and C (which were stirred for 24 hours), Formula A (which was stirred for 4 hours) demonstrated a lower average loading efficiency.

TABLE 1

Buprenorphine loading efficiency of buprenorphine/PLGA nanoparticles (n = 3)

| Formula (drug:polymer) | Average Loading efficiency (%) | Standard Deviation |
|---|---|---|
| A (1:16) | 28.46 | 3.11 |
| B (1:16) | 49.57 | 5.82 |
| C (1:8) | 70.69 | 1.80 |

EXAMPLE 5

Loading Efficiency of Buprenorphine/PLA Nanoparticle Compositions

The loading efficiency of buprenorphine in the nanoparticle compositions can be analyzed. In this example, buprenorphine/PLA nanoparticle compositions were evaluated.

The loading efficiency of buprenorphine/PLA nanoparticle compositions was also analyzed by HPLC. Two buprenorphine/PLA nanoparticle samples were evaluated: Formula B (drug:polymer ratio 1:16), and Formula C (drug:polymer ratio 1:8).

The HPLC system was composed of a reverse phase C-18 column (Phenomenex, Torrance, Calif.) with a UV detector (wavelength: 210 nm). The mobile phase was contained 80% acetonitrile and 20% phosphate buffer (pH 6) and the flow rate was 1 ml/min. Two mg of buprenorphine/PLA lyophilized nanoparticles were dissolved in 4 mL of acetonitrile and analyzed at different time intervals using HPLC. The loading efficiency was determined by comparing the observed buprenorphine amount in the nanoparticles to the original amount of drug added. Each formulation of nanoparticles was analyzed in triplicate. Results are shown in Table 2.

TABLE 2

Buprenorphine loading efficiency of buprenorphine/PLA nanoparticles (n = 3)

| Formula (drug:polymer) | Average Loading efficiency (%) | Standard Deviation |
|---|---|---|
| B (1:16) | 12.60 | 1.20 |
| C (1:8) | 26.00 | 2.40 |

EXAMPLE 6

Particle Size Evaluation of Stable Nanoparticle Compositions

The particle size of the nanoparticle compositions can be evaluated. In this example, both buprenorphine/PLGA and buprenorphine/PLA nanoparticle compositions were evaluated. A Nicomp 380 ZLS Zeta Potential/Particle Sizer (Nicomp, New York, N.Y.) was used to determine the cumulative average particle size for the three formulations of nanoparticles.

For the buprenorphine/PLGA nanoparticles, three different samples were evaluated: Formula A (drug:polymer ratio 1:16), Formula B (drug:polymer ratio 1:16), and Formula C (drug:polymer ratio 1:8). Results are shown in Table 3. Compared with Formulas B and C (which were stirred for 24 hours), Formula A (which was stirred for 4 hours) demonstrated a larger average particle size.

TABLE 3

Average particle size of buprenorphine/PLGA nanoparticles

| Formula (drug:polymer) | Average Diameter (nm) | Standard Deviation | Polydispersity Index (PI) | n |
|---|---|---|---|---|
| A (1:16) | 4802.8 | 2664.4 | 0.31 | 2 |
| B (1:16) | 436.3 | 257.7 | 0.35 | 2 |
| C (1:8) | 351.78 | 193.2 | 0.31 | 4 |

For the buprenorphine/PLA nanoparticles, two different samples were evaluated: Formula B (drug:polymer ratio 1:16) and Formula C (drug:polymer ratio 1:8). Results are shown in Table 4.

TABLE 4

Average particle size of buprenorphine/PLA nanoparticles

| Formula (drug:polymer) | Average Diameter (nm) | Standard Deviation | Polydispersity Index (PI) | n |
|---|---|---|---|---|
| B (1:16) | 227.4 | 43.8 | 227.4 | 3 |
| C (1:8) | 222.8 | 52.9 | 222.8 | 3 |

EXAMPLE 7

Dissolution Evaluation of Buprenorphine/PLGA Nanoparticle Compositions

The dissolution of the nanoparticle compositions can be evaluated in vitro. In this example, the dissolution of buprenorphine/PLGA nanoparticles was analyzed. Three different samples were evaluated: Formula A (drug:polymer ratio 1:16), Formula B (drug:polymer ratio 1:16), and Formula C (drug:polymer ratio 1:8).

Two (2) mg of buprenorphine/PLGA nanoparticles was added to 25 mL PBS, (pH 7.4) containing 0.1% sodium lauryl sulfate, with constant shaking at 37° C. The concentration of buprenorphine released from the nanoparticles was measured at 4 hours, 24 hours, 3 days, 6 days, 10 days, and 15 days. One mL of PBS was removed from the media of each sample and was filtered with a 0.45 μm pore size syringe filter and analyzed by HPLC. One mL fresh dissolution medium was then added back to each sample in order to maintain 25 mL in each sample vial. The cumulative amount of buprenorphine release was compared to amount loaded into the nanoparticle compositions according to the loading efficiency (see Example 4).

Figure 4:
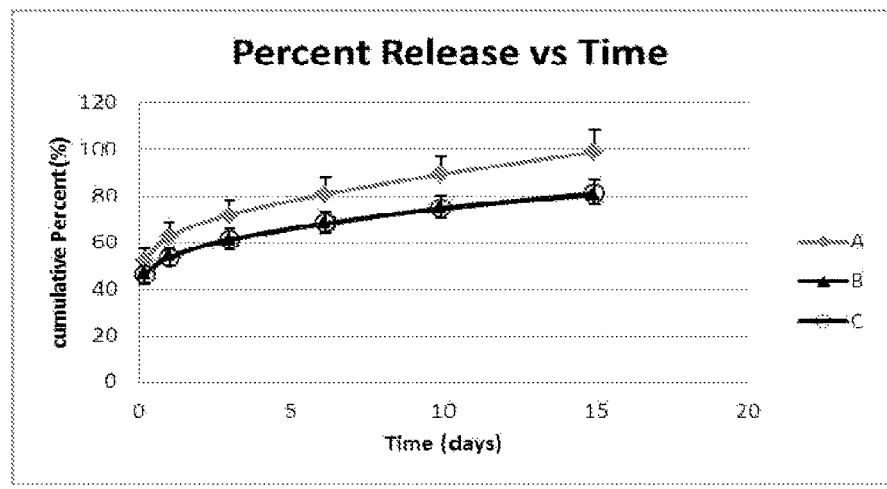
FIG. 4 shows the cumulative release of buprenorphine (%) from buprenorphine/PLGA nanoparticles over time (days). Three different samples were evaluated: Formula A (drug:polymer ratio 1:16), Formula B (drug:polymer ratio 1:16), and Formula C (drug:polymer ratio 1:8).

Results are shown in FIG. 4, which displays the cumulative release of buprenorphine (%) from the nanoparticles over time (days). As demonstrated in FIG. 4, the buprenorphine/PLGA nanoparticles displayed an initial rapid release of buprenorphine followed by a slow release of buprenorphine which extended for 15 days or longer. Particle size of the nanoparticles affected the results of drug release. The release of the buprenorphine/PLGA nanoparticles showed a linear release profile after the initial rapid release. Surprisingly, the linear release profile of the buprenorphine/PLGA nanoparticles in Formula B (drug:polymer ratio 1:16) and in Formula C (drug:polymer ratio 1:8) was essentially identical (see FIG. 4). Furthermore, the preparations comprising nanoparticle compositions of smaller size (i.e., Formula B and C) surprisingly displayed slower release of buprenorphine compared to the preparation comprising nanoparticle compositions of larger size (i.e., Formula A), which was formulated by a slightly different method.

EXAMPLE 8

Dissolution Evaluation of Buprenorphine/PLA Nanoparticle Compositions

The dissolution of the nanoparticle compositions can be evaluated in vitro. In this example, the dissolution of buprenorphine/PLA nanoparticles was analyzed. Two different samples were evaluated: Formula B (drug:polymer ratio 1:16) and Formula C (drug:polymer ratio 1:8).

Two (2) mg of buprenorphine/PLA nanoparticles was added to 25 mL PBS, (pH 7.4) containing 0.1% sodium lauryl sulfate. The dissolution vials were placed into an autobath set to 37° C. at 58 shakes per minute, simulating conditions found in the human body.

The concentration of buprenorphine released from the nanoparticles was measured at 4 hours, 24 hours, 2 days, 5 days, 9 days, 12 days, 15 days, and 19 days. Each sample was centrifuged before 10 mL of PBS was removed from the media and filtered with a 0.45 µm pore size syringe filter and analyzed by HPLC. Ten (10) mL of fresh dissolution medium was then added back to each sample in order to maintain 25 mL in each sample vial. The cumulative amount of buprenorphine release was compared to amount loaded into the nanoparticle compositions according to the loading efficiency (see Example 5).

Figure 5:
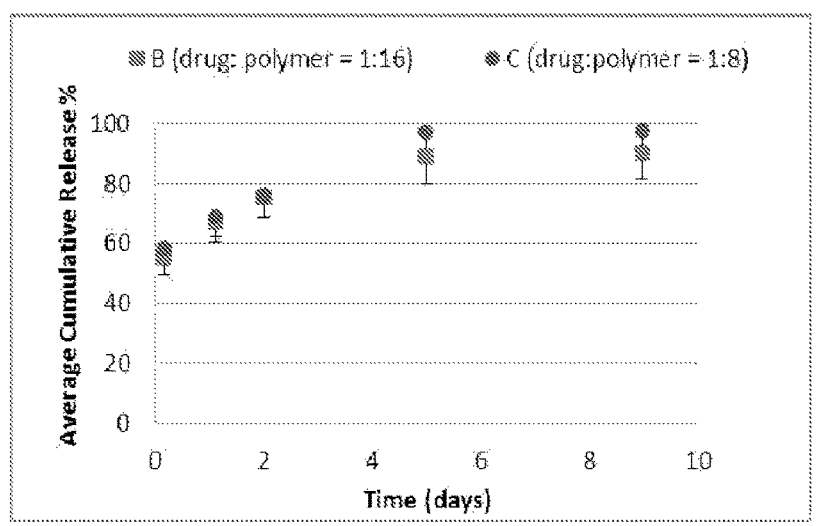
FIG. 5 shows the cumulative release of buprenorphine (%) from buprenorphine/PLA nanoparticles over time (days). Two samples were evaluated: Formula B (drug:polymer ratio 1:16) and Formula C (drug:polymer ratio 1:8).

Results are shown in FIG. 5, which displays the cumulative release of buprenorphine (%) from the nanoparticles over time (days). As demonstrated in FIG. 5, the buprenorphine/PLA nanoparticles displayed an initial rapid release of buprenorphine followed by a slow linear release of buprenorphine which extended for about 7 days. The release of the buprenorphine/PLA nanoparticles showed a linear release profile. Surprisingly, the linear release profile of the buprenorphine/PLA nanoparticles in Formula B (drug:polymer ratio 1:16) and in Formula C (drug:polymer ratio 1:8) was similar (see FIG. 5).

EXAMPLE 9

In Vivo Evaluation of Stable Nanoparticle Compositions

An in vivo analysis of the buprenorphine nanoparticle compositions to evaluate the comparative bioavailability (rate and extent of absorption) of the nanoparticle compositions can be evaluated in Sprague-Dawley rats (Harlan Laboratories, Indianapolis, Ind.). Adjusting the release rate of buprenorphine, utilizing controlled release dosage forms of buprenorphine nanoparticles, can potentially produce long lasting analgesic effects in animals and limit side effects in the animals. Such formulations could advantageously provide an alternative to currently available dosage forms that require frequent oral or parenteral administration.

In this example, a urinary collection bioavailability/pharmacokinetic study of the rats can be performed. The urinary evaluation may be advantageous compared to a blood sampling study for various reasons. For example, previous studies suggest that 27% of buprenorphine is excreted unchanged in the urine and, thus, is an excellent candidate for urinary pharmacokinetic studies. Furthermore, a multiple blood sampling over 1-2 weeks could be stressful and compromise animal health with high failure rates. Moreover, plasma concentrations of buprenorphine are typically very low, and can be difficult or to measure in animals based on available analytical techniques without large volume blood draws.

In this example, six (6) different formulations of buprenorphine nanoparticle compositions can be produced and evaluated. All materials utilized for production of the nanoparticle compositions have been previously approved by the FDA. The particle size and the morphology of the nanoparticle compositions can be evaluated as described in the previous examples. In addition, the buprenorphine content of the nanoparticle compositions and their encapsulation efficiency can be determined. The in vitro release (dissolution) in PBS (pH 7.4) at 37° C. can be investigated using HPLC methods as described in the previous examples.

Based on the drug releasing profiles observed with the nanoparticle compositions, two formulations showing one-week release profiles and one formulation displaying a two-week release profile can be selected for in vivo evaluation in rats. Each formulation of buprenorphine nanoparticle composition can be studied after either subcutaneous (SC) or intramuscular (IM) administration to the rats.

The in vivo release profile of buprenorphine nanoparticles can be evaluated by comparing the buprenorphine concentrations, the buprenorphine amounts, and the excretion rates of buprenorphine in the urine of rats. Forty eight (48) male Sprague-Dawley rats (approximate body weight 200 grams (g)±25 g can be evaluated in the present example, comprising 8 total groups of 6 rats per group.

Evaluations can be made to compare the various buprenorphine nanoparticle formulations and also compared to multiple injections of a commercial immediate release injectable (Buprenex® (which contains buprenorphine hydrochloride at 0.324 mg per mL (Reckitt Benckiser, United Kingdom)) as a control. The dose of Buprenex® for rats is based on Plumb's Veterinary Drug Handbook (6th Edition, Pharma Vet Inc. Stockholm, Wis. (2008)).

All nanoparticles can be sterilized by gamma irradiation before injection into the experimental animals in this study. Rats can be housed at a Biological Research Facility, with food and water available ad libitum. The metabolic cage can be cleaned and autoclaved before use and the area in metabolic cage can be 70 in$^2$ per rat. Rats can be housed in groups or pairs until placed in the metabolic cages. Once in the metabolic cages, they should be singly housed in order to prevent comingling of urine from different animals. Daily food and water intakes can be recorded. In order to collect urinary excretion accurately, every rat can be kept in one cage for 7 days and then be moved to a clean autoclaved cage for 7 additional days. The night before the experiment (Day 1), urine can be collected from each rat in the urinary cup at the bottom of the cage (Time 0, baseline).

Each formulation of buprenorphine nanoparticle compositions can be studied following either subcutaneous (SC) or intramuscular (IM) administration to the rats. The various groups of rats can be evaluated in either a one-week release study or a two-week release study. A list of treatments, dosing, and biological sampling is shown below in Table 5:

TABLE 5

In vivo study groups of buprenorphine nanoparticle compositions

| Study | Group | Drug | Route | No. of rats | No. of injection | Sample | No. of samples (per Day) |
|---|---|---|---|---|---|---|---|
| One week | Control | Buprenex | IM | n = 6 | 13 (=2 × 6.5) | Urine | 7 samples (Day 1)<br>2 samples (Day 2-Day 14) |
| | | | SC | n = 6 | 13 (=2 × 6.5) | Urine | 7 samples (Day 1)<br>2 samples (Day 2-Day 14) |

TABLE 5-continued

In vivo study groups of buprenorphine nanoparticle compositions

| Study | Group | Drug | Route | No. of rats | No. of injection | Sample | No. of samples (per Day) |
|---|---|---|---|---|---|---|---|
| | Treatment A | Formulation A | IM | n = 6 | 1 only | Urine | 7 samples (Day 1)<br>2 samples (Day 2-Day 14) |
| | | | SC | n = 6 | 1 only | Urine | 7 samples (Day 1)<br>2 samples (Day 2-Day 14) |
| | Treatment B | Formulation B | IM | n = 6 | 1 only | Urine | 7 samples (Day 1)<br>2 samples (Day 2-Day 14) |
| | | | SC | n = 6 | 1 only | Urine | 7 samples (Day 1)<br>2 samples (Day 2-Day 14) |
| Two weeks | Treatment C | Formulation C | IM | n = 6 | 1 only | Urine | 7 samples (Day 1)<br>2 samples (Day 2-Day 21) |
| | | | SC | n = 6 | 1 only | Urine | 7 samples (Day 1)<br>2 samples (Day 2-Day 21) |

One Week Release Study:
For Control Group Receiving Buprenex®:

On the day of the experiment (8:00 AM, Day 1), rats in the control group (n=6 rats in IM group and n=6 rats in SC group; total 12 rats) can be administered 100 µL of Buprenex® buprenorphine hydrochloride (equivalent to buprenorphine dose of 0.15 mg/kg for a 200 g rat) via a 25 gauge, ⅝ inch needle in the right hind leg (IM) or at the back of neck (SC). Urine samples can be collected at 2, 4, 6, 8, and 12 hours after the first injection. At 8:05 PM of Day 1, a second dose of Buprenex® can be administered in the left hind leg (IM) or the back of neck (SC) and urine collected from 12-24 hours. Scheduled administration of Buprenex® can be repeated as described for 6.5 days. Injection sites can be rotated between two hind legs or the neck areas. From Day 2 to Day 7, urine samples can be collected twice a day prior to the injections. On Day 7, after urine sample is collected at 144 hours (8:00 AM), the last dose of Buprenex® can be given. From Day 8 to Day 14, no drug can be administered but urine collection samples can continue to be taken twice a day until the end of the 14 day period. The concentration of buprenorphine in the urine can be analyzed by an enzyme-linked immunosorbent assay (ELISA) (Neogen Cop. (Lexington, Ky.)). From the evaluated drug concentrations and urine volumes, the drug excretion rates and cumulative amounts can be determined for relative bioavailability comparisons. Muscle tissue surrounding the injection site can be inspected by microscope for irritation after rat is sacrificed at the end of the study.

For Treatment Groups Receiving Buprenorphine Nanoparticle Compositions:

Rats in treatment groups (n=6 rats in Treatment A IM group; n=6 rats in Treatment A SC group; n=6 rats in Treatment B IM group; n=6 rats in Treatment B SC group; total=24 rats) can receive a single dose of either IM or SC injection of a buprenorphine nanoparticle composition containing 1.95 mg/kg (0.15 mg/kg×2×6.5 day=1.95 mg/kg). The night before the experiment, each rat can be caged in a metabolic cage and urine can be collected (Time 0, baseline). On the day of experiment (8:00 AM, Day 1), rats can be given one single IM or SC injection of nanoparticles in 100 uL via 25 gauge, ⅝ inch needle in the right hind leg (IM) or injection at the back of neck (SC). Urine samples can be collected at 2, 4, 6, 8, 12, and 24 hour following drug administration. From Day 2 to Day 14, urine samples can be collected twice a day.

On Day 14, after urine sample is collected, rats can be sacrificed. The tissue surrounding the injection sites can be inspected by microscope to evaluate the tissue reaction to the nanoparticles of the treatment group. The microscopic results from each group can then be compared.

Two Weeks Release Study:
For Control Group Receiving Buprenex®:

In order to limit animal use and discomfort, it is possible to test no additional rats in the control group for the two week studies. Instead, the results of one week drug excretion and release in this control group can be used to extrapolate to two week profiles.

For Treatment Groups Receiving Buprenorphine Nanoparticle Compositions:

Rats in treatment groups (n=6 rats in Treatment C IM group; n=6 rats in Treatment C SC group; total=12 rats) can receive a single dose of either IM or SC injection of a buprenorphine nanoparticle composition containing 4.05 mg/kg (0.15 mg/kg×2×13.5 day=4.05 mg/kg). The night before the experiment, each rat can be caged in a metabolic cage and urine can be collected (Time 0, baseline). On the day of experiment (8:00 AM, Day 1), rats can be given a single IM or SC injection of the nanoparticle formulation in 100 µL via 25 gauge, ⅝ inch needle in the right hind leg (IM) or at the back of neck (SC). Urine samples can be collected at 2, 4, 6, 8, 12, and 24 hour following drug administration. From Day 2 to Day 21, urine samples can be collected twice a day.

In order to ensure the health of animals, the daily food intake and water consumption of every rat can be recorded and compared to the control group during the entire experimental period.

Buprenorphine is a relatively safe analgesic and causes less toxic effects than morphine and heroin. However, if any infection or sickness such as necrosis or swelling at injection site is observed in rats during this example, the project veterinarian can be consulted and early euthanasia may be performed.

What is claimed is:

1. A stable nanoparticle composition comprising buprenorphine and at least one biodegradable polymer,
   wherein the stable nanoparticle composition has a release profile of buprenorphine of between 7 days and 28 days,
   wherein the buprenorphine and the polymer are present at a ratio of buprenorphine:polymer between 1:4 and 1:10,
   wherein the release profile is a linear release profile; and
   wherein the stable nanoparticle composition has a size between about 10 nm and about 500 nm.

2. The stable nanoparticle composition of claim 1, wherein the biodegradable polymer is selected from the group consisting of polycaprolactone (PCL), polyglycolic acid (PGA), poly(DL)-lactide (PLA), poly(DL)-lactide-co-glycolide (PLGA), or mixtures thereof.

3. The stable nanoparticle composition of claim 1, wherein the biodegradable polymer is PLA.

4. The stable nanoparticle composition of claim 1, wherein the biodegradable polymer is PLGA.

5. The stable nanoparticle composition of claim 1, wherein the stable nanoparticle composition has a release profile of buprenorphine of between 14 days and 28 days.

6. The stable nanoparticle composition of claim 1, wherein the release profile of the stable nanoparticle composition is a linear release profile after initial rapid release.

7. A method of controlling pain in an animal comprising administering to the animal in need thereof a therapeutically effective amount of a stable nanoparticle composition comprising buprenorphine and at least one biodegradable polymer,
wherein the stable nanoparticle composition has a release profile of buprenorphine of between 7 days and 28 days,
wherein the buprenorphine and the polymer are present at a ratio of buprenorphine:polymer between 1:4 and 1:10,
wherein the release profile is a linear release profile, and
wherein the stable nanoparticle composition has a size between about 10 nm and about 500 nm.

8. The method of claim 7, wherein the biodegradable polymer is PLA.

9. The method of claim 7, wherein the biodegradable polymer is PLGA.

10. The method of claim 7, wherein the administration of the stable nanoparticle composition is via a subcutaneous parenteral formulation.

11. The method of claim 7, wherein the administration of the stable nanoparticle composition is via an intramuscular parenteral formulation.

12. A pharmaceutical formulation comprising a therapeutically effective amount of a stable nanoparticle composition,
wherein stable nanoparticle composition comprises buprenorphine and at least one biodegradable polymer,
wherein the stable nanoparticle composition has a release profile of buprenorphine of between 7 days and 28 days,
wherein the buprenorphine and the polymer are present at a ratio of buprenorphine:polymer between 1:4 and 1:10,
wherein the release profile is a linear release profile, and
wherein the stable nanoparticle composition has size between about 10 nm and about 500 nm.

13. The pharmaceutical formulation of claim 12, wherein the biodegradable polymer is PLA.

14. The pharmaceutical formulation of claim 12, wherein the biodegradable polymer is PLGA.

15. The pharmaceutical formulation of claim 12, wherein the stable nanoparticle composition has a release profile of buprenorphine of between 14 days and 28 days.

16. The pharmaceutical formulation of claim 12, wherein the release profile of the stable nanoparticle composition is a linear release profile after initial rapid release.

17. The pharmaceutical formulation of claim 12, wherein the stable nanoparticle composition is administered as a single dose.

18. The stable nanoparticle composition of claim 1, wherein the ratio of buprenorphine:polymer is selected from the group consisting of about 1:4, about 1:5, about 1:8, and about 1:10.

19. The method of claim 7, wherein the ratio of buprenorphine:polymer is selected from the group consisting of about 1:4, about 1:5, about 1:8, and about 1:10.

20. The pharmaceutical formulation of claim 12, wherein the ratio of buprenorphine:polymer is selected from the group consisting of about 1:4, about 1:5, about 1:8, and about 1:10.

* * * * *